United States Patent
André et al.

(10) Patent No.: US 11,638,723 B2
(45) Date of Patent: May 2, 2023

(54) METHOD FOR GENERATING T CELLS PROGENITORS

(71) Applicants: Assistance Publique—Hopitaux de Paris, Paris (FR); Fondation Imagine—Institut des Maladies Génétiques, Paris (FR); Université Paris Cité, Paris (FR); Institut National de la Santé et de la Recherche Médicale (INSERM), Paris (FR)

(72) Inventors: Isabelle André, Issy les Moulineaux (FR); Marina Cavazzana, Paris (FR); Kuiying Ma, Paris (FR); John Tchen, Pantin (FR); Tayebeh-Shabi Soheili, Paris (FR); Ranjita Devi Moirangthem, Paris (FR)

(73) Assignees: Assistance Publique—Hopitaux de Paris, Paris (FR); Fondation Imagine—Institut des Maladies Génétiques, Paris (FR); Université Paris Cité, Paris (FR); Institut National de la Santé et de la Recherche Médicale (INSERM), Paris (FR)

( * ) Notice: Subject to any disclaimer, the term of this patent is extended or adjusted under 35 U.S.C. 154(b) by 0 days.

(21) Appl. No.: 17/173,632

(22) Filed: Feb. 11, 2021

(65) Prior Publication Data

US 2021/0169934 A1 Jun. 10, 2021

Related U.S. Application Data

(60) Division of application No. 17/010,208, filed on Sep. 2, 2020, now Pat. No. 11,426,430, which is a continuation of application No. 16/485,488, filed as application No. PCT/EP2018/053406 on Feb. 12, 2018.

(30) Foreign Application Priority Data

Feb. 13, 2017 (EP) .................................. 17305161

(51) Int. Cl.
| | | |
|---|---|---|
| C12N 5/00 | (2006.01) | |
| C12N 15/63 | (2006.01) | |
| C12N 5/02 | (2006.01) | |
| A61K 35/17 | (2015.01) | |
| C12N 5/0783 | (2010.01) | |
| A61K 31/70 | (2006.01) | |

(52) U.S. Cl.
CPC ............ *A61K 35/17* (2013.01); *C12N 5/0636* (2013.01); *C12N 2501/125* (2013.01); *C12N 2501/145* (2013.01); *C12N 2501/2307* (2013.01); *C12N 2501/25* (2013.01); *C12N 2501/26* (2013.01); *C12N 2501/42* (2013.01); *C12N 2506/11* (2013.01); *C12N 2533/52* (2013.01)

(58) Field of Classification Search
CPC ................. A61K 35/17; C12N 5/0636; C12N 2501/125; C12N 2501/145; C12N 2501/2307; C12N 2501/25; C12N 2501/26; C12N 2501/42; C12N 2501/11; C12N 2533/52
See application file for complete search history.

(56) References Cited

U.S. PATENT DOCUMENTS

| | | | |
|---|---|---|---|
| 6,093,531 A | 7/2000 | Bjornson et al. | |
| 10,543,257 B2 | 1/2020 | Uchida et al. | |
| 2011/0052554 A1* | 3/2011 | Zakrzewski | ............ A61P 35/00 424/93.71 |
| 2013/0095079 A1 | 4/2013 | Bernstein et al. | |
| 2014/0349402 A1* | 11/2014 | Cooper | .......... A61K 39/001119 435/455 |
| 2014/0369973 A1 | 12/2014 | Bernstein et al. | |
| 2017/0128556 A1 | 5/2017 | Kawamoto et al. | |
| 2017/0158749 A1 | 6/2017 | Cooper et al. | |
| 2019/0142867 A1 | 5/2019 | Zandstra et al. | |

FOREIGN PATENT DOCUMENTS

| | | |
|---|---|---|
| JP | 2012508188 A | 4/2012 |
| JP | 2016526913 A | 9/2016 |
| RU | 2535966 C2 | 12/2014 |
| WO | 1999028486 A1 | 6/1999 |
| WO | 2010031006 A1 | 3/2010 |
| WO | 2010051634 A1 | 5/2010 |
| WO | 2011068962 A1 | 6/2011 |
| WO | 2014110353 A1 | 7/2014 |
| WO | 2015017755 A1 | 2/2015 |

(Continued)

OTHER PUBLICATIONS

Salima Hacein-Bey et al. Optimization of retroviral gene transfer protocol to maintain the lymphoid potential of progenitor cells. Human gene therapy 12:291-301, (Year: 2001).*

(Continued)

*Primary Examiner* — Quang Nguyen
(74) *Attorney, Agent, or Firm* — Panitch Schwarze Belisario & Nadel LLP; Erin M. Dunston

(57) ABSTRACT

The invention relates to an in vitro method to generate T cell progenitors, comprising the step of culturing CD34+ cells in a medium containing TNF-alpha and/or an antagonist of the Aryl hydrocarbon/Dioxin receptor, in particular StemRegenin 1 (SR1), in presence of a Notch ligand and optionally a fibronectin fragment.

5 Claims, 8 Drawing Sheets
Specification includes a Sequence Listing.

(56) References Cited

FOREIGN PATENT DOCUMENTS

| WO | 2015099134 A1 | 2/2015 |
| --- | --- | --- |
| WO | 2016055396 A1 | 4/2016 |
| WO | 2016205680 A1 | 12/2016 |

OTHER PUBLICATIONS

Ohishi et al., "The Notch ligand, Delta-1, inhibits the differentiation of monocytes into macrophages but permits their differentiation into dendritic cells", Blood, Sep. 2001, vol. 98, No. 5; pp. 1402-1407.

Reimann et al., "Human T-Lymphoid Progenitors Generated in a Feeder-Cell-Free Delta-Like-4 Culture System Promote T-Cell Reconstitution in NOD/SCID/γc-/- Mice", Stem Cells, Aug. 2012, vol. 30, No. 8, pp. 1771-1780.

Awong et al., "Characterization in vitro and engraftment potential in vivo of human progenitor T cells generated from hematopoietic stem cells", Blood, Jul. 2009, vol. 114, pp. 972-982.

Awong et al., "Human proT-cells generated in vitro facilitate hematopoietic stem cell-derived T-lymphopoiesis in vivo and restore thymic architecture", Blood, Dec. 2013, vol. 122, No. 26, pp. 4210-4219.

Gehre et al., "A stromal cell free culture system generates mouse pro-T cells that can reconstitute T-cell compartments in vivo", European Journal of Immunology, Mar. 2015, vol. 45, No. 3, pp. 932-942.

Gori et al., "Efficient generation, purification, and expansion of CD34(+) hematopoietic progenitor cells from nonhuman primate-induced pluripotent stem cells", Blood, Sep. 2012, vol. 120, No. 13, pp. e35-e44.

Thordardottir et al., "The aryl hydrocarbon receptor antagonist StemRegenin 1 promotes human plasmacytoid and myeloid dendritic cell development from CD34+ hematopoietic progenitor cells", Stem Cells and Development, May 2014, vol. 23, No. 9, pp. 955-967.

Brauer et al., "T Cell Genesis: In Vitro Veritas Est?", Trends in Immunology, Dec. 2016, vol. 37, No. 12, pp. 889-901.

Shukla et al., "Progenitor T-cell differentiation from hematopoietic stem cells using Delta-like-4 and VCAM-1", Nature Methods, May 2017, vol. 14, No. 5, pp. 531-538.

Cavazzano-Calvo et al., "Hématopoïèse humaine : des cellules CD34 aux lymphocytes T", Medecine/Sciences, 2006; vol. 22, pp. 151-159.

Yuan et al., "Lin28b reprograms adult bone marrow hematopoietic progenitors to mediate fetal-like lymphopoiesis", Science, Mar. 2012, vol. 335, No. 6073, pp. 1195-1200.

Lansdorp et al., "Ontogeny-related changes in proliferative potential of human hematopoietic cells", Journal of Experimental Medicine, Sep. 1993, vol. 178, No. 3, pp. 787-791.

Szilvassy et al., "Differential homing and engraftment properties of hematopoietic progenitor cells from murine bone marrow, mobilized peripheral blood, and fetal liver", Blood, Oct. 2001, vol. 98, No. 7, pp. 2108-2115.

Frassoni et al., "Cord blood transplantation provides better reconstitution of hematopoietic reservoir compared with bone marrow transplantation", Blood, Aug. 2003, vol. 102, No. 3, pp. 1138-1141.

Liang et al., "Effects of aging on the homing and engraftment of murine hematopoietic stem and progenitor cells", Blood, Aug. 2005, vol. 106, No. 4, pp. 1479-1487.

Six et al., "A human postnatal lymphoid progenitor capable of circulating and seeding the thymus", Journal of Experimental Medicine, Dec. 2007, vol. 204, No. 13, pp. 3085-3093.

Weinmaster et al., "Notch signal transduction: a real rip and more", Current Opinion in Genetics and Development, Aug. 2000, vol. 10, No. 4, pp. 363-369.

Kueh et al., "Asynchronous combinatorial action of four regulatory factors activates Bcl11b for T cell commitment", Nat Immunology, Aug. 2016, vol. 17, No. 8, pp. 956-965.

Dik et al., "New insights on human T cell development by quantitative T cell receptor gene rearrangement studies and gene expression profiling", Journal of Experimental Medicine , Jun. 2005, vol. 201, No. 11, pp. 1715-1723.

Cardin and Weintraub, "Molecular modeling of protein-glycosaminoglycan interactions", Arteriosclerosis, Jan.-Feb. 1989, vol. 9, No. 1, pp. 21-32.

Wayner et al., "Identification and characterization of the T lymphocyte adhesion receptor for an alternative cell attachment domain (CS-1) in plasma fibronectin", Journal of Cell Biology, Sep. 1989, vol. 109, No. 3, pp. 1321-1330.

Kimizuka et al., "Production and characterization of functional domains of human fibronectin expressed in *Escherichia coli*", Journal of Biochemistry, Aug. 1991, vol. 110, No. 2, pp. 284-291.

Chono et al., "Removal of inhibitory substances with recombinant fibronectin-CH-296 plates enhances the retroviral transduction efficiency of CD34(+)CD38(−) bone marrow cells", Journal of Biochemistry, Sep. 2001, 130(3): 331-334.

Varnum-Finney et al., "Immobilization of Notch ligand, Delta-1, is required for induction of notch signaling", Journal of Cell Science, Dec. 2000, vol. 113, No. 23, pp. 4313-4318.

Jonuleit et al., "Pro-inflammatory cytokines and prostaglandins induce maturation of potent immunostimulatory dendritic cells under fetal calf serum-free conditions", European Journal of Immunology, Dec. 1997, vol. 27, No. 12, pp. 3135-3142.

Luft et al., "Type I IFNs enhance the terminal differentiation of dendritic cells", Journal of Immunology, Aug. 1998, vol. 161, No. 4, pp. 1947-1953.

Boitano et al., "Aryl hydrocarbon receptor antagonists promote the expansion of human hematopoietic stem cells", Science, Sep. 2010, vol. 329, No. 5997, pp. 1345-1348.

Six et al., "Cytokines and culture medium have a major impact on human in vitro T-cell differentiation", Blood Cells Molecules and Diseases, Jun. 2011, vol. 47, No. 1, pp. 72-78.

Kim and Roy, "Ligand-functionalized biomaterial surfaces: controlled regulation of signaling pathways to direct stem cell differentiation", Biological interactions on materials surfaces, May 2009, pp. 157-171.

Huijskens et al., "Technical advance: ascorbic acid induces development of double-positive T cells from human hematopoietic stem cells in the absence of stromal cells", Journal of Leukocyte Biology, Dec. 2014, vol. 96, No. 6, pp. 1165-1175.

Lamers et al., "Retronectin-assisted retroviral transduction of primary human T lymphocytes under good manufacturing practice conditions: tissue culture bag critically determines cell yield", Cytotherapy, 2008, vol. 10, No. 4, pp. 406-416.

Reimann et al., "In vitro Generation of Human T-Cell Precursors From Bone Marrow CD34+ Cells by Short Exposure to Immobilized Notch-Ligand Delta-Like 4." Blood (2009) 114 (22): 3532.

Ohishi Kohshi et al., "Delta-1 enhances marrow and thymus repopulating ability of human CD34+CD38− cord blood cells", The Journal of Clinical Investigation, Oct. 2002, vol. 110, No. 8, pp. 1165-1174.

Snoeck Hans-W et al., "Tumor necrosis factor alpha is a potent synergistic factor for the proliferation of primitive human hematopoietic progenitor cells and induces resistance to transforming growth factor beta but not to interferon gamma", The Journal of Experimental Medicine, Feb. 1, 1996, 183(2) pp. 705-710.

Weekx Steven F A et al., "Generation of T cells from adult human hematopoietic stem cells and progenitors in a fetal thymic organ culture system: stimulation by tumor necrosis factor-alpha", Blood, May 1, 2000, 95(9) pp. 2806-2812.

Jaleco A.C. et al., "Differential effects of Notch ligands Delta-1 and Jagged-1 in human lymphoid differentiation" J Exp Med. Oct. 1, 2001;194(7):991-1002. doi: 10.1084/jem.194.7.991.

Smits et al. "Tumor necrosis factor promotes T-cell at the expense of B-cell lymphoid development from cultured human CD34+ cord blood cells" Experimental Hematology 35. 2007, 1272-1278.

Besseyrias et al. "Hierarchy of Notch-Delta interactions promoting T cell lineage commitment and maturation" J. Exp. Med. 2007, 204(2):331-43.

(56) References Cited

OTHER PUBLICATIONS

Dos Santos Schiavinato et al. "TNF-alpha and Notch signaling regulates the expression of HOXB4 and GATA3 during early T lymphopoiesis" In Vitro Cell.Dev.Biol.—Animal. 2016, 52:920-934.

Dahlberg et al. "Ex vivo expansion of human hematopoietic stem and progenitor cells" Blood. 2011, 117(23):6083-90.

Delaney et al. "Notch-mediated Expansion of Human Cord Blood Progenitor Cells Capable of Rapid Myeloid Reconstitution" Nat Med. 2010, 16(2): 232.

Hozumi et al. "Delta-like 4 is indispensable in thymic environment specific for T cell development" J. Exp. Med. 2008, vol. 205 No. 11 2507-2513.

Koch et al. "Delta-like 4 is the essential, nonredundant ligand for Notch1 during thymic T cell lineage commitment" J. Exp. Med. 2008, vol. 205 No 11 2515-2523.

Smith et al. "In Vitro T-Cell Generation From Adult, Embryonic, and Induced Pluripotent Stem Cells: Many Roads to One Destination" Stem Cells 2015, 33:3174-3180.

Feng et al. "Expansion of engrafting human hematopoietic stem/progenitor cells in three-dimensional scaffolds with surface-immobilized fibronectin" J Biomed Mater Res A., Sep. 15, 2006; 78(4): 781-791.

Ross A. Kopher et al., "Human embryonic stem cell-derived CD34+ cells function as MSC progenitor cells", Bone, 2010, 47(4), pp. 718-728.

Milliano et al., "Initial signaling of the fibronectin receptor ($\alpha 5\beta 1$ integrin) in hepatic stellate cells is independent of tyrosine phosphorylation" Journal of Hepatology vol. 39, Issue 1, Jul. 2003, pp. 32-37.

Yanase et al., "Lysophosphatidic Acid Enhances Collagen Gel Contraction by Hepatic Stellate Cells: Association with Rho-Kinase" BBRC vol. 277, Issue 1, Oct. 14, 2000, pp. 72-78.

Wihelath et al., "Fibronectin promotes VEGF-induced CD34+ cell differentiation into endothelial cells" Journal of vascular surgery vol. 39, Issue 3, Mar. 2004, pp. 655-666.

Reimann et al., "Further Characterization of T-Cellular Precursors Generated From CD34+ Progenitors by Exposure to Immobilized Notch Ligand Delta-Like 4 In Vitro." Blood, American society of Hematology, Nov. 2010, p. 3712.

* cited by examiner

A

B

METHOD FOR GENERATING T CELLS PROGENITORS

CROSS-REFERENCE TO RELATED APPLICATIONS

This application is a Divisional Application of U.S. patent application Ser. No. 17/010,208, filed on Sep. 2, 2020, which is a Continuation Application of U.S. patent application Ser. No. 16/485,488, filed on Aug. 13, 2019, which is a U.S. National Stage patent application pursuant to 35 U.S.C. § 371 of International Patent Application PCT/EP2018/053406, filed on Feb. 12, 2018, and published as WO 2018/146297 on Aug. 16, 2018, which claims priority to European Patent Application 17305161.6 filed on Feb. 13, 2017, all of which are incorporated herein by reference in their entireties for all purposes.

The invention relates to the field of cell therapy, in particular of hematopoietic stem cells graft, transformed or not, and more particularly of immune reconstitution after such graft.

Graft of progenitor and Hematopoietic Stem/Progenitor Cell (HSPC) is considered the best therapeutic option for the most severe hereditary immune deficiencies, for many malignant hemopathies, as well as for a number of solid tumors.

Currently, in allograft situations with partial HLA incompatibility, the injections, to previously conditioned recipients, of increasing doses of sorted CD34+ HSPC allows donor transplantation with effective prevention of graft-versus-host disease (GVH). Nevertheless, the differentiation of new T lymphocytes from the injected CD34+ cells requires a minimum period of 4 months and these T lymphocytes are in sufficient number to play a protective role against infections only a few months after their appearance.

This slowness of immune reconstitution leads to numerous infectious complications especially viral, but also to relapses, which influence the long-term prognosis of the grafted patients.

In addition, other therapeutic protocols use a gene therapy approach, namely an autograft of transduced HSPC, which has been shown to be effective in the treatment of certain hereditary immune deficiencies. The advantage of this strategy over HSPC CD34+ allogeneic transplantation is indisputable in terms of survival and morbidity when no HLA-compatible donor is available. Nevertheless, clinical experience has shown that, for some patients with severe infections, reconstitution of the T lymphocyte compartment is slow and never reaches normal levels of circulating T lymphocytes. The morbidity and mortality associated with this particular context are important.

Because of the high morbidity and mortality associated with this type of transplant, the development of novel therapies to reduce the immunodeficiency period after transplantation is fully justified.

In particular, it is important to accelerate the generation of T lymphocytes by the administration of precursors already engaged in the T lymphocyte differentiation pathway (T cell progenitors).

These T cell precursors are obtained from CD34+ HSPC differentiation and have in particular the CD7+ marker, which is a marker of differentiation in the T-cell pathway. They may also have other markers. Awong et al (Blood 2009; 114: 972-982) described the following precursors of T lymphocytes: early thymic progenitor (ETP), which have markers (CD34+/CD45RA+/CD7+), precursor cells at the proT1 stage (CD7++/CD5−), precursor cells at the proT2 stage (CD7++/CD5+), and cells at the preT stage (CD7++/CD5+ CD1a+). The HSPC acquire these markers in a successive way when passing from one stage to the other, over the T cell development pathway. It is further known that in humans, the CD1a antigen distinguishes the passage from a very immature thymic progenitor to a progenitor clearly engaged in the T-pathway (Cavazzana-Calvo et al, MEDECINE/SCIENCES 2006; 22: 151-9).

A T-cell precursors transplant, concomitant with HSPC grafting, would allow the rapid production of a mature and functional T lymphocyte compartment and thus help prevent the risk of severe infections by allowing the patient to benefit from some immunity before complete reconstitution of the immune system.

Moreover, it is important to be able to use adult cells rather than cord blood cells, since it is easier and cheaper to obtain adult cells than cord blood cells and since adult cells are more commonly used in allograft.

However, data published in the literature, obtained in humans and mice, show intrinsic differences between fetal hematopoietic cells (including cord blood) and adult cells. These differences relate to survival, the ability to repair DNA damage, proliferative capacity and potential to differentiate (see, for example, Yuan et al., (2012 Mar. 9; 335 (6073): 1195-200), which Indicate that adult bone marrow cells are less effective than fetal cells in their potential to generate a variety of cell types: Lansdorp et al (J Exp Med 1993 Sep. 1; 178 (3): 787-91); Szilvassy et al (Blood, 2001 Oct. 1, 98 (7): 2108-15), Frassoni et al (Blood, 2003 Aug. 1, 102 (3): 1138-41), Liang et al. 106 (4): 1479-87), Six et al (J Exp Med 2007 Dec. 24, 204 (13): 3085-93)).

WO 2016/055396 describes that it is possible to generate T-cell precursors by culturing CD34+ cells in presence of an immobilized ligand of Notch (in particular the soluble domain of the Delta-like-ligand, fused to a Fc region of an IgG protein), and of a fragment of a fibronectin, containing the RGDS (SEQ ID NO: 3, Arginine-Glycine-Aspartate-Sérine) and CS-1 domains, as well as the heparin-binding domain (in particular in the presence of Retronectin®). The Notch ligand used may be referred to as DL4/Fc.

It is to be noted that this document discloses that presence of both the immobilized ligand of Notch, and the fibronectin makes it possible to increase generation of T lymphocytes progenitors (CD7+ cells), which was already an improvement in the art, but that the percentage of CD7+CD34− cells remains quite low, as shown in FIG. 3 of WO 2016/055396. It is however interesting and particularly important to increase this percentage, in order to be able to administer a higher amount of precursor to the patient in need thereof. On the other hand, it is also important that the cells remains at a early stage of differentiation to be able to provide a proper immunity.

It is reminded that Notch proteins are transmembrane receptors that regulate the cellular response to a large number of environmental signals. In mammals, four Notch (Notch 1-4) receptors and five ligands (Delta-like-1, 3, and 4, Jagged1, Jagged2) have been described (Weinmaster Curr Opin Genet Dev 2000: 10: 363-369).

The Delta-like-ligand 4 can be designated as:
 (ii) Delta-like-ligand 4 (corresponding to the name of the DLL4 gene)
 (iii) Delta-like-4 or Delta ligand 4 (abbreviation DL-4).

In the present application, the Notch Delta-like-1 and Delta-like-4 ligands may be designated respectively by DL1 and DL4 or by DL-1 and DL-4. The sequences of ligands DL-1 and DL-4 are specified as SEQ ID NO: 1 and SEQ ID NO: 2, respectively.

Ohishi et al (BLOOD, vol. 98, no. 5, 2001, pp 1402-1407) relates to the effect of Notch signaling on monocyte differentiation into macrophages and dendritic cells. The monocyte cells used in the experiments disclosed in this document were either peripheral blood monocytes purified by negative selection, or monocytes obtained after in vitro differentiation of CD34+ stem cells. The cells used in this document have thus entered the monocyte/macrophage/dendritic cells differentiation pathway, have lost the CD34 marker (which is a hematopoietic stem cell marker) and present the CD14 marker. These cells are cultured in presence of the extracellular domain of Delta-1 and GM-CSF, TNF-alpha (which is used to induce the differentiation of CD34+ cell-derived CD1a−CD14+ cells into dendritic cells). This document this doesn't uses CD34+ cells in presence of a Notch ligand and of TNF-alpha and doesn't pertain to the generation of T-cell precursors (CD7+ T lymphocytes precursors).

SHUKLA et al (NATURE METHODS, vol. 14, no. 5, 2017, 531-538) and WO 2017/173551 disclose a method for generating progenitor T cells from stem and/or progenitor cells comprising exposing the stem and/or progenitor cells to Notch ligand Delta-like-4 (DL4) and vascular adhesion molecule 1 (VCAM-1).

The method described in the present application allows the generation and the increase (proliferation) of number of CD7+ T lymphocyte precursors, from CD34+ stem cells, without using a cell stroma (which can't be easily envisaged in a clinical context). Furthermore, the method is particularly adapted when performed with CD34+ cells issued from adult donors.

Furthermore, the cells obtained through the process as herein disclosed, harbor the Bcl11b marker, which is important transcriptional factor uniquely switched on since T-cell commitment (Kueh et al, 2016, Nat Immunol. 2016 August; 17(8):956-65. doi: 10.1038/ni.3514).

The inventors have also shown absence of rearrangement of the T cell receptors loci (either TCRbeta, TCRgamma or TCRdelta) in the progenitors obtained through the process herein disclosed.

Moreover, a decrease in apoptosis markers was shown, for the precursors herein obtained, as compared to the process disclosed in WO 2016/055396.

In summary, the process herein disclosed makes it possible to obtain a number of T cell precursors high enough to be efficiently used for an adult receiving a stem cells transplant.

This method may also be used to obtain transformed (transduced) T cell precursors for gene therapy, when a vector containing a gene of interest is used at some point during the process herein disclosed.

The cells obtained by the process herein disclosed can be obtained for adult CD34+ cells, and can be used for allogenic grafts or autografts, even when cord blood cells are used for such grafts.

It is to be noted that the method, although very efficient for adult CD34+ cells, may also be used with cord blood CD34+ cells.

In a particular embodiment, the method herein disclosed thus fasten T-cell generation in vivo after injection of T-cell progenitors produced from HSPC in an in vitro culture system, combining an immobilized fusion protein derived from the Notch ligand, Delta-4, Retronectin® and a combination of cytokines.

This system allows, within 7 days, the generation of T-cell progenitors that are phenotypically and molecularly similar to human thymic T-cell precursors. Furthermore, these T-cell progenitors are able to give rise human mature and diverse T-cell in NSG mice, with a faster kinetic as compared to HSPC.

The results herein reported were obtained from both cord blood (CB) and adult (mobilized peripheral blood, mPB from adult donors) HSPC.

The inventors have shown that the amount of T cell precursors can be improved from CD34+ cells by exposing said CD34+ cells to a Notch ligand and in the presence of the soluble TNF-alpha (Tumor Necrosis Factor Alpha, Uniprot P01375, RefSeq NP_000585, SEQ ID NO: 8). Said exposure is made under conditions suitable to generate progenitor T cells. Optionally, the cells are also exposed to a fibronectin fragment containing an RDGS motif, and/or a CS-1 motif and optionally a heparin binding domain. Preferably, said fibronectin fragment contains an RDGS motif, a CS-1 motif and a heparin binding domain.

TNF is primarily produced as a 233-amino acid-long type II transmembrane protein arranged in stable homotrimers. The secreted form of human TNF-alpha takes on a triangular pyramid shape, and weighs around 17-kDa.

As disclosed in WO 2016/055396, it is possible to perform the method herein disclosed, using a RGDS peptide and/or a CS-1 peptide in place of the fibronectin fragment. A combined use of the RGDS and CS-1 peptides is preferred, in particular fused in the same protein. Thus, the RGDS and/or CS-1 peptides may be present as such in the culture medium or within a polypeptide or protein present in the culture medium. When the culture medium only contains the RGDS and/or CS-1 peptide as such, one can relate to these as "free" peptide(s) in the culture medium if such peptides are not immobilized on the inner surface of the culture vessel. Indeed, the peptide(s) may be in solution or immobilized on the inner surface of the vessel in which the CD34+ cells are exposed to the immobilized Notch ligand.

However, as indicated above, it is preferred to use a fragment of fibronectin, which contains the RGDS and CS-1 patterns, as well as a heparin-binding domain. The fibronectin fragment may be free in solution or immobilized on the inner surface of the culture container.

The process is performed in vitro, in a container, such as a cell culture plate (Petri dish, 24 well array or the like), preferably with the Notch ligand immobilized on its inner surface. The Notch ligand may, however, be immobilized on any other support present in the culture medium, such as on the surface of beads (in particular microbeads). Immobilization of the Notch ligand is essentially intended to stabilize the ligand, in order to allow activation of the Notch receptor of the CD34+ cells.

By "T cell progenitor", one intends to designate any cell involved in the differentiation pathway to the T lymphoid pathway from a CD34+ HSPC. This cell is therefore characterized in that it expresses the CD7 marker, which is known to be one of the earliest markers during the lymphopoiesis of the T cells. Depending on the state of differentiation in the T lymphoid pathway, it can express or not the CD34 marker (loss of CD34 during differentiation). Such T cell progenitor may also express or not the CD5 marker.

Among the "T-cell progenitors" are those cells which can be found in the post-natal thymus, i.e. early thymic progenitor (ETP) (CD34+/CD45RA+/CD7+), proT1 cells (CD34+CD45RA+CD7++CD5−CD1a−), proT2 cells (CD34+CD45RA+CD7++CD5+CD1a−) and preT cells (CD34−CD7++/CD5+CD1a+). T-cell receptor (TCR) loci rearrange in a highly ordered way (TCRδ-TCRγ-TCRβ-TCRα). To note, the first functional TCR rearrangements occurs at the CD34−CD7++/CD5+CD1a+ preT cell stage (Dik et al. J Exp Med 2005; 201:1715-1723). T-cell progenitors are well known in the state of the art. They are cited in particular by Reimann et al (STEM CELLS 2012; 30:1771-1780.) and by Awong et al (2009, op.cit.).

The term "RGDS peptide" is intended to designate any peptide or protein that contains the RGDS pattern, so that it can bind integrin VLA-5. Such peptide or protein can be tested for its ability to bind VLA-5 integrin by methods known and reported in the art. RGDS peptide binds to integrin VLA-5 (Very Late Antigen-5), which is a dimer composed of CD49e (alpha5) and CD29 (beta1).

Heparin-binding domains are known in the art and present in numerous proteins that bind to heparin. Their sequence is generally XBBXBX or XBBBXXBX (B=acide aminé basique; X=acide aminé hydropathique; Cardin and Weintraub, Arterioscler Thromb Vasc Biol. 1989; 9:21-32, SEQ ID NO: 4 et SEQ ID NO: 5).

Presence of such a heparin-binding domain is particularly favorable when the CD34+ cells are exposed to a viral (especially a retroviral) vector in order to transduce them and obtain T cell progenitors expressing a transgene.

A CS-1 peptide or CS-1 pattern is a 25 amino acids peptide (DELPQLVTLPHPNLHGPEILDVPST, SEQ ID NO: 6), described by Wayner et al, 1989, J. Cell Biol. 109: 1321). This CS-1 pattern binds to the VLA-4 (Very Late Antigen-4) receptor. This antigen is a dimer integrin, composed of CD49d (alpha 4) and CD29 (beta 1).

In a particular embodiment, the fibronectin fragment is present in the culture medium or immobilized on the inner (in particular the bottom) wall of the container. Fibronectin is a protein, which in its natural form is a v-shaped large dimer of 100 nm long and 460 kDa. The two monomers are connected by two disulfide bridges at their C-terminus. The term "fibronectin" or "fibronectin fragment" is understood to mean the natural fibronectin protein (i.e. any isoform produced by alternative splicing), but also a monomer of this protein, or a fragment of this protein (but containing the peptide RGDS, as well as CS-1 peptide and heparin binding site).

A fibronectin which is particularly suitable for carrying out the process herein disclosed is Retronectin®. This protein corresponds to a fragment of a human fibronectin (CH-296 fragment, Kimizuka et al., J Biochem., 1991 August 110 (2):284-91, Chono et al., J Biochem 2001 September 130 (3):331-4) and contains the three functional domains that are preferred for implementation of the method (the cell-binding C domain containing the RGDS peptide, the heparin-binding domain and the CS-1 sequence). This protein is sold in particular by the company Takara Bio Inc. (Shiga, Japan).

In a particular embodiment, the fibronectin fragment is immobilized (i.e. bound to a solid support and is not present free in solution (although it is possible that certain elements may be found in solution)). This solid support is preferably the bottom wall of the container in which the process is carried out. However, it is also possible to envisage binding the fibronectin fragment to beads, such as polymer or magnetic beads (with a diameter generally comprised between 1 and 5 μm). The binding of the protein or peptide to these beads may or may not be covalent. Methods for attaching a protein or peptide to the beads are known in the art. It is also possible to introduce the fibronectin fragment into a semisolid medium, such as agar or gel.

When the fibronectin fragment is immobilized on the support (in particular the bottom wall of the container in which the process is performed), this immobilization may also be covalent or not. In a preferred embodiment, this immobilization is carried out non-covalently by allowing the fibronectin fragment to be absorbed onto the glass or plastic composing the bottom wall of the container.

In a particular embodiment, as seen above, the differentiation of the CD34+ cells into T-cell progenitors is carried out together with the transduction or transfection (including Nucleofection™, a specific electroporation system developed by Lonza) of the CD34+ cells by means of a vector (such as a viral vector or a nucleic acid fragment such as a plasmid or plasmidic RNA or DNA sequences) in order to introduce a gene of interest (or a system for gene editing) in these cells. This means that the cells exposed to the Notch ligand and the fibronectin fragment, with TNF-alpha, are also exposed to a viral supernatant for at least part of their time of exposure to the Notch ligand and fibronectin fragment, with TNF-alpha.

The teachings of WO 2016/055396 with regards to the operative conditions for performing cell transduction are expressly applicable to the present method and are thus considered as being expressly recited in this application.

One can cite, in particular:
(iv) Exposure of the cells to the Notch ligand, fibronectine fragment and TNF-alpha, for some time (preferably more than 4 hours, more preferably more than 6 h, or more than 8 h or 10 h, but less than 36 h, more preferably less than 30 h or less than 24 h) with appropriate cytokines known in the art and disclosed in WO 2016/055396, and addition of the viral supernatant for an appropriate duration (preferably more than 4 hours, more preferably more than 6 h, 8 h or 10 h, and preferably less than 30 hours, more preferably less than 24 h, more preferably around 16 h).
(v) Second transduction if required as taught in WO 2016/055396
(vi) Use of this protocol for autologous hematopoietic stem cells grafts in gene therapy protocols, in order for the transgene to add a protein that is absent or deficient in the patient so as to bring a therapeutic benefit.
(vii) Usable transgenes: gene correcting immunodeficiencies (in particular severe combined immunodeficiencies SCID or not, CID), HIV, X-linked adrenoleukodystrophy, hemoglobinopathies, in particular β-thalassemy or sickle cell disease. One can also use, as the transgene, a gene that codes for a Chimeric Antigen Receptor (CAR), i.e. a cell surface protein that recognizes a cell surface protein that is specifically expressed by cancer cells in order to trigger immune response against the cancer cells through the engineered CAR-T cells
(viii) Preferred use of a viral supernatant to allow insertion of the transgene within the cell genome, using in particular lentiviruses known, and described in the art.
(ix) Introduction of the viral vector in the cell culture medium after pre-activation of the CD34+ cells between 4 and 36 h, preferably between 6 and 24 h
(x) Exposure of the cells to the viral vector between 4 and 30 h, preferably between 12 and 24 h, more preferably around 16 h, and removal of the viral vector (harvesting and washing the cells, and resuspending these cells in presence of the Notch ligand, the fibronectin fragment and the TNF-alpha).

As indicated above, in another embodiment, the CD34+ cells are exposed to a system making it possible to perform gene editing. Such systems are now widely known and described in the art and are essentially based on nucleic acid double-break repair. Such genome editing system may use a nuclease selected from the group consisting of meganucleases, zinc finger nucleases (ZFNs), transcription activator-like effector-based nucleases (TALEN), and CRISPR-Cas nucleases. The fact that the CD34+ cells proliferate during exposure to the elements as recited above, and thus in presence of TNF-alpha, makes it possible to use these gene editing systems that require proliferation of cells.

In a particular embodiment, the Notch ligand is the Delta-like-1 protein (SEQ ID NO: 1) or a fragment thereof (soluble domain).

In another and preferred embodiment, the Notch ligand is the Delta-like-4 protein (SEQ ID NO: 2).

In a particular embodiment, said Notch ligand is a fusion protein comprising the soluble domain of a natural Notch ligand fused to an Fc region of an IgG protein. As known in the art, the soluble domain of a Notch ligand represents the extracellular portion of said ligand. Varnum-Finney et al (J Cell Sci., 2000 December; 113 Pt 23:4313-8) described a fusion protein of the soluble part of DL-1 with an Fc portion of IGg1. Reimann et al (op cit) described a fusion protein of the soluble part of DL-4 (amino acids 1-526) with the Fc fragment of an IgG2b immunoglobulin. It is thus preferred when the IgG protein is an IgG2. In a preferred embodiment, the sequence of the Notch ligand used in the method herein disclosed is SEQ ID NO: 7. A commercially available product (Sino Biologicals) comprising the extracellular domain (Met 1-Pro 524) of human DLL4 (full-length DLL4 accession number NP_061947.1) fused to the Fc region of human IgG 1 at the C-terminus is a DL4 protein is also suitable for use herein.

The culture medium used in the context of the method herein disclosed is any medium adapted for culturing CD34+ cells and T cells. Mention may in particular be made of α-MEM, DMEM, RPMI 1640, IMDM, BME, McCoy's 5A, StemSpan™, in particular SFII (StemCell Technologies) media or Fischer's medium. StemSpan™ SFII medium contains, in particular, Iscove's MDM, Bovine serum albumin, Recombinant human insulin, Human transferrin (iron-saturated), 2-Mercaptoethanol.

A suitable and preferred culture medium for carrying out the process herein disclosed is the X-VIVO™ medium (Lonza, Basel, Switzerland). This medium was used in particular by Jonuleit et al (Eur J Immunol, 1997, 27, 12, 3135-42) and Luft et al (J Immunol, 1998, 161, 4, 1947-53).

Preferably, a basal medium is used (i.e., which a medium that allows the growth of the cells without the need to add supplements), in which, however, one preferably would add serum, and/or growth factors and cytokines.

Thus, fetal bovine serum (FBS) or fetal calf serum (FCS), autologous human serum or human AB serum is preferably added to the basal culture medium. Preferably, this medium is supplemented with at least 15% of fetal serum, more preferably at least 20%. The FBS is particularly suitable for the implementation of the process. In particular, it is preferred to use defined FBS. The defined FBS is a high-quality serum which has been analyzed and filtered to avoid the presence of viral particles. It is sold as such by many suppliers, such as the HyClone™ Defined Fetal Bovine Serum (FBS) of Thermo Scientific™.

In addition to TNF-alpha, the culture medium is also preferably complemented with cytokines and growth factors. These cytokines and growth factors are especially selected from the group consisting of SCF (stem cell factor), thrombopoietin (TPO, also called megakaryocyte growth and development factor, MGDF), Flt3-Ligand (which is a growth factor Hematopoietic), interleukin 3 (IL-3), interleukin 7 (IL-7) and SCF (stem cell factor). In a particular embodiment, the culture medium contains at least three, preferably at least four of these cytokines or growth factors, in addition to TNF-alpha.

In a preferred embodiment, and in particular for the generation of T cell precursors that are not transduced with a viral vector, at least or exactly three cytokines are added. Preferably, these three cytokines are Interleukin-7 (IL-7), SCF (Stem Cell Factor) and Flt-3 Ligand (hematopoietic growth factor).

In another preferred embodiment, four cytokines, i.e. the three cytokines mentioned above and TPO (thrombopoietin) are added.

In another particular embodiment, and in particular for the generation of T cell precursors transduced with a viral vector, the nature of the cytokines and growth factors can be varied during the implementation of the method.

Thus, IL-3, IL-7, SCF, TPO, and Flt3-L can be used in the medium if the step of pre-activating the cells prior to addition of the viral vector, and then supplement the medium only with IL-7, SCF, TPO, and Flt3-L after the vector is removed.

The aforementioned cytokine and growth factor mixtures are sufficient to induce the differentiation of CD34+ cells into T-cell precursors and generally the culture medium comprises no other cytokine or growth factor, except TNF-alpha, which, as described in the examples, makes it possible to increase the number of T cell precursors.

In the process herein foreseen, the total duration of exposure of the CD34+ cells in the presence of the Notch ligand, of the protein or peptide exhibiting the RGDS motif and of TNF-alpha, is generally carried out for a time preferably of more than 3 days and less than 10 days.

This exposure may vary depending on whether the cells are transduced. Thus, an exposure time of three days may be sufficient for adult stem cells not transduced, whereas it will generally be longer for infantile stem cells (about 7 days) or when transduction is performed.

CD34+ cells are obtained from a bone marrow puncture, from umbilical cord blood or from peripheral blood from adult donors, which have been mobilized particularly with G-CSF or any other mobilizing agent known in the art. Methods for sorting CD34+ cells are known in the art. In particular, magnetic beads having an antibody recognizing CD34 on their surface can be used for this purpose.

Preferably, the cell culture vessel is prepared by immobilizing the Notch ligand and the fibronectin fragment on the inner (preferably the lower) surface prior to exposing the CD34+ cells. Retronectin® or other fibronectin naturally adhere to the plastic of the cell culture box (Petri dish or 24-well box, or other). Similarly, if Notch ligand is used as a fusion protein with the Fc fragment of an immunoglobulin, this Fc fragment also adheres to the plastics. It is therefore sufficient to leave the container in the presence of these compounds for a few hours in order to obtain the appropriate coating. A method to coat such culture container with the Notch ligand and the fibronectin fragment is disclosed in details in WO 2016/055396 and can be applied for implementing the method as herein disclosed.

It is reminded that, according to WO 2016/055396, around 75% of DL-4 will adhere to the container surface when 5 μg/ml is used, the optimal dose being higher or equal to 1.25 μg/ml and preferably between 2.5 and 5 μg/ml.

With regards to the fibronectin fragment, a concentration of 25 μg/ml is particularly adapted (especially when Retronectin® is used), although one can use other concentrations (higher or lower).

In the implementation of the process herein disclosed, CD34+ cells are added at a concentration comprised between $10^6$ et $10^7$ cells/ml, in particular around $2\times10^6$ CD34+ cells/ml in the culture vessel.

Depending on whether the cells are to be transduced and of the CD34+ cells, one can use a plate of between 2 to 10 $cm^2$ (i.e. a plate from 24 to 6 wells). When one uses a 24 wells plate, one adds between $10^4$ and $10^6$ CD34+ cells in each well, preferably from $2\times10^4$ to $4\times10^5$ CD34+ cells per well. When a 6 well plate is used, one will add between $8\times10^4$ and $2\times10^6$ cells per well.

The quantity of cells to add is adapted by the person skilled in the art, according to the container used.

The cells are placed in the well, in the selected basal medium, supplemented with TNF-alpha, and preferentially supplemented with growth factors and cytokines, as indicated above.

The concentrations of cytokines or growth factors are between 2 and 300 ng/ml. Preferably, the concentration is higher than 40 ng/l and lower than 300 ng/ml or 200 ng/l, more preferably around 100 ng/ml.

However, when one wishes to generate transduced T cell progenitors, and when the cells are pre-activated before being exposed to the viral vector, one can use higher concentrations (around 300-400 ng/ml). In this embodiment, SCF and Flt3-L can be used at des concentrations in the range of 300 ng/ml, TPO and IL-7 in the range of 100 ng/ml, and IL-3 at about 40 ng/ml.

TNF-alpha is preferably used at a concentration equal or higher than 5 ng/ml. Indeed, as demonstrated in the examples, this low concentration is enough to obtain the proliferation of the T cell precursors, without modifying the differentiation pathway.

However, higher concentrations can also be used. In particular, the TNF-alpha concentration can be as high as 300 ng/ml or 200 ng/ml. An appropriate concentration is around 100 ng/ml. However, other concentrations such as 10 ng/ml, 20 ng/ml or 50 ng/ml are also suitable.

The invention thus relates to an in vitro method for generating T cells precursors comprising the step of culturing CD34+ cells in a suitable medium comprising TNF-alpha and in the presence of an immobilized Notch ligand, and optionally the fibronectin fragment as disclosed above.

The invention thus relates to an in vitro method for expanding T cells precursors comprising the step of culturing CD34+ cells in a suitable medium comprising TNF-alpha and in the presence of an immobilized Notch ligand, and optionally the fibronectin fragment as disclosed above.

Expanding the T cells precursors is intended to mean that there are more T cell precursors than when the TNF-alpha is not used, and/or that there are more T cell precursors than the number of CD34+ cells introduced in the container.

In particular, the T cells precursors obtained by the above methods are CD34−/CD7+/CD5− precursors.

Generally, the cells don't harbor the CD1a marker either.

In a preferred embodiment, the T cells precursors obtained by the above methods are CD34−/CD7+/CD1a− precursors.

This means that the population of T cell precursors obtained by the present method express the CD7 marker, and that more than 80% of the cells expressing this marker have the above phenotype (not expressing CD34 and CD1a, or CD34 and CD5, or CD34 and CD1a and CD5), as analyzed by flow cytometry. This phenotype is generally obtained after 7 days of culture.

As indicated, the CD34+ cells are preferably not cord blood cells. However, the method may also be used with and is applicable to cord blood CD34+ cells, and it also leads to improved results.

The method is particularly interesting when implemented with CD34+ cells that have been isolated from an adult patient. Said patient may be a healthy donor, or a donor with a disease, and particularly for which the cells will be corrected by viral transduction.

The cells may be cultured for more than 3 days, and preferably for at least 5 days, more preferably for at least or exactly 6 days, most preferably for at least or exactly 7 days, although the duration of culture may last longer.

In the method herein disclosed, TNF-alpha is preferably added to the culture medium from day 0 (i.e. at the beginning of CD34+ cells culture) and shall remain present, in the culture medium, for at least three days, and preferably during all the time the cells are culture (i.e. preferably about 7 days).

When performing the method herein disclosed, it is possible to further add StemRegenin 1 (SR1, 4-(2-(2-(Benzo[b]thiophen-3-yl)-9-isopropyl-9H-purin-6-ylamino)ethyl) phenol, CAS 1227633-49-10) in the culture medium already containing the TNF-alpha.

The invention also relates to a method for obtaining T cells progenitors, comprising the steps of a. performing the method as disclosed above and b. purifying the generated T cells progenitors thereby obtained.

Purification may be performed by washing the cells and resuspending such in a basal medium.

This method may also comprise the step of conditioning the T cells progenitors in a pouch for injection to a patient.

In this case, it is preferred when these cells are reconditioned in a saline solution containing 5% HSA such as Albunorm™ 5% 50 g/L (Octopharma, Lingolsheim, France).

These cells may also be frozen according to methods known in the art.

The invention also relates to a pouch for intravenous injection, containing a population of T cells progenitors (susceptible to be obtained or as obtained by a method as described above), among which the proportion of CD7+ cells in this population is higher than 80%, more preferably higher than 85%.

The invention also relates to a pouch for intravenous injection, containing a population of CD7+ T cells progenitors (susceptible to be obtained or as obtained by a method as described above), where the proportion of CD34− and CD5− cells (cells that are CD7+ and both CD34− and CD5−) in this population is higher than 80%, more preferably higher than 85%.

The invention also relates to a pouch for intravenous injection, containing a population of CD7+ T cells progenitors (susceptible to be obtained or as obtained by a method as described above), where the proportion of CD34− cells (cells that are CD7+ and CD34−) in this population is higher than 50%, more preferably higher than 60%. Furthermore, at least 80%, and more preferably at least 85% of the cells in this population are CD1a− cells.

The invention also relates to an in vitro method for obtaining transformed T-cells progenitors, comprising the steps of a. culturing CD34+ cells in a suitable medium comprising TNF-alpha and in the presence of an immobilized Notch ligand b. exposing the cells to a vector intended for transfection or transduction of CD34+ cells.

As disclosed above, and after steps of washing and culturing again the cells, transformed T-cells progenitors (expressing a transgene, integrated within their genome) are obtained.

The invention also relates to an in vitro method for obtaining modified T-cells progenitors, comprising the steps of
a. culturing CD34+ cells in a medium comprising TNF-alpha and in the presence of an immobilized Notch ligand
b. exposing the cells to a vector or a nucleic acid sequence containing the element appropriate for gene editing at least for some time during cell culture.

Thereby T cells progenitors modified by gene editing are obtained, after potential steps of washing and culturing.

The invention also relates to T cells progenitors, in particular as obtained by the method herein disclosed, for their use in an immunosuppressed patient, in particular for allowing immune reconstitution in this patient and/or obtaining an immune protection against infections in said patient, during a period of some months (at least two months, preferably at least six months).

In a particular embodiment, the patient is an immunosuppressed patient. The reasons for the deficiency may be multiple: hereditary immune deficiency, chemotherapy for leukemia, conditioning, graft containing only stem cells, post-graft treatment for prophylaxis of GVH (graft-versus-host disease), age of patient, and complications such as infections.

In particular, the patient can be immunosuppressed due to the depletion of its immune cells following therapy before hematopoietic stem cells transplantation.

In this embodiment, the graft may be an allograft (in this case, the T cell progenitors are preferably derived from a partially HLA-compatible donor), or an autograft (in which case the T cell progenitors have preferentially being transformed by a vector in order to express a gene and/or a protein making it possible to correct a genetic defect in said patient).

The T cell progenitors are preferably a population of CD7+ cells (i.e. a population where at least 75%, more preferably at least 80% of cells in the population express the CD7 marker). This population is also part of the invention. In particular, it is susceptible to be obtained by a method herein disclosed. In a specific embodiment, it is obtained by a method herein disclosed.

More specifically, the T cell progenitors are preferably a population of CD7+ cells (i.e. a population where at least 75%, more preferably at least 80% of cells in the population express the CD7 marker) where the proportion of CD34- and CD5-cells (cells that are CD7+ and both CD34- and CD5-) in this population is higher than 80%, more preferably higher than 85%. This population is also part of the invention. In particular, it is susceptible to be obtained by a method herein disclosed. In a specific embodiment, it is obtained by a method herein disclosed.

In another embodiment, the T cell progenitors are preferably a population of CD7+ cells (i.e. a population where at least 75%, more preferably at least 80% of cells in the population express the CD7 marker). In this population, more than 50%, more preferably more than 60% of cells don't express the CD34 marker. In this population at least 80%, more preferably at least 85% of cells don't express the CD1a marker. The proportion of CD7+ CD1a- cells in this population is preferably at least 80%. This population is also part of the invention. In particular, it is susceptible to be obtained by a method herein disclosed. In a specific embodiment, it is obtained by a method herein disclosed.

In order to determine whether a cell is positive or not to a surface marker (CD7, CD34, CD5 or CD1a), one shall use any method known in the art, and in particular flow cytometry, after the cells have been marked with fluorescent antibodies directed against the surface antigen. The principle is that a signal will be emitted, for each cell of the population, with a given intensity, and cells are considered as positive for the antigen if the signal is higher than a given threshold.

For CD34: a control population consisting of a population of HPSC (such as one isolated from cord blood or from mobilized peripheral blood) is used to determine the appropriate thresholds. In this population of cells, the cells are CD34+ CD7- CD5-, or CD34+ CD7- CD1a-. With this control, it is possible to determine threshold for each antigen that will be used to determine whether cells in another population are positive or not for these antigens.

The control population generally will contain around 90% of CD34+ CD7- CD5-, or of CD34+ CD7- CD1a- hematopoietic stem cells. The threshold is the signal intensity level for which the cells of the population can be sorted in a 90/10 proportion.

For CD7 (resp. CD5 or CD1a): a control population is used, obtained by isolation of Peripheral Blood Mononuclear Cell (PBMC) by any technique known in the art, and in particular a density gradient technique such as Ficoll-Paque PLUS (GE Healthcare Life Sciences). CD7 (resp. CD5 or CD1a) positive cells are isolated using any technique known in the art such as the MACS® technique (Magnetic Cell Isolation and Cell Separation, Miltenyi Biotec) which uses magnetic beads with anti-CD7 (resp. anti.CD5 or anti-CD1a) antibody. In this population, the cells will essentially be CD7+ (resp. CD5+ or CD1a+), it is believed that the proportion would be around 90/10.

The thresholds for assessing whether a cell is positive to a surface antigen are determined using the control population for this antigen, and would be the intensity for which more than 90% of the cells of the control population have a higher signal intensity.

Consequently, a cell is considered as being positive for an antigen if the intensity signal for this antigen is higher than the threshold as determined above, and negative for the antigen if the intensity signal for this antigen is lower than the threshold as determined above.

The fact that the vast majority of T cell progenitors in the population don't express the CD1a marker may prove to be favorable, as cells expressing this CD1a marker may not be very efficient to reach the thymus and may thus be as efficient as CD1a- cells for in vivo repopulation. Since the reconstitution potential of CD1a+ cells is uncertain, it is thus preferable to lower the amount of such cells in the population.

The invention also relates to a method for treating an immunosuppressed patient, in particular for the purpose of allowing an immune reconstitution, at least temporarily, in this patient, comprising the step of administering to said patient T-cell progenitors, as described above.

This method may also include the step of obtaining such progenitors by exposing CD34+ cells to a Notch ligand in the presence of TNF-alpha (as described above) and preferably to a protein or peptide having the RGDS motif and/or the CS1 motif, in particular A fibronectin fragment as described above, under the conditions mentioned above.

In particular, a therapeutically effective amount is administered, that is to say of the order of 1 to $5 \times 10^6$ of progenitors per kg, which makes it possible to provide the patient with cells capable of playing a protective role with regard to infections during a few months (of the order of about 6 months).

Preferably, this administration of T cell progenitors is performed just prior to, just after or concomitantly with a hematopoietic stem cell transplant in said patient. As seen above, the injected cells can be transformed by a vector intended to allow the correction of a genetic defect in said patient.

In another embodiment, the T cell progenitors are injected to a patient that doesn't need a hematopoietic stem cell transplant. Indeed, it is possible to use the transformed or transduced T cells progenitors to treat some immunodeficiencies, in which only T cells are affected, HIV or cancer patients (using the progenitors modified to lead to CAR-T cells), without the need to perform the immune system depletive chemotherapy.

It is to be noted that the teachings of the invention, as disclosed with TNF-alpha are also applicable with the purine derivative StemRegenin 1 (SR1, disclosed in Boitano et al, Science. 2010 Sep. 10; 329(5997):1345-8). Thus SR1 can be substituted to TNF-alpha (i.e. used in place of TNF-alpha) to obtain T cell progenitors from CD34+ cells, with a beginning of differentiation, and expansion of the cells (increase in the number of cells). The concentration of SR1 is preferably in the range of 750 nM (30 ng/ml), also higher concentration such as 1500 nM or 2500 nM (100 ng/ml), or even 5000 nM (200 ng/ml) or lower such as 500 nM (20 ng/ml) can also be envisaged. When used alone, but particularly in combination with TNF-alpha, much lower concentrations can be used, as low as 3 ng/ml, or 10 ng/ml. Suitable concentrations also include 30 ng/ml or 100 ng/ml. Consequently, any concentration higher than 3 ng/ml, or higher than 10 ng/ml is suitable to increase the differentiation of the CD34+ cells to T-cells progenitors.

SR1 is a ligand (an antagonist) of the Aryl hydrocarbon/Dioxin receptor (AhR). Other AhR antagonists can be used alone, or in combination with TNF-alpha, to promote differentiation of CD34+ cells into the T-cell progenitor lineage. One can cite resveratrol, omeprazole, Luteolin, alpha-naphthoflavone, mexiletine, tranilast, 6,2',4'-Trimethoxyflavone, CH 223191 (1-Methyl-N-[2-methyl-4-[2-(2-methylphenyl)diazenyl]phenyl-1H-pyrazole-5-carboxamide, CAS 301326-22-7). The amount of AhR antagonist is to be determined on a case-by-case basis by one of skill in the art, taking into consideration the IC50 of the antagonist (SR1 has an IC50 of 127 nM, whereas CH 223191 has an IC50 of 30 nM) and the fact that some products may have an agonist activity towards the AhR when used at high concentrations (such as alpha-naphthoflavone) or depending of the cellular context (such as omeprazole). In view of the difference in IC50 between SR1 and CH 223191, it is foreseen that an effective concentration of CH 223191 would be well below the effective concentration of SR1, herein disclosed.

Consequently, the invention also relates to
(i) an in vitro method for generating T cells precursors, comprising the step of culturing CD34+ cells in a medium comprising an antagonist of the Aryl hydrocarbon/Dioxin receptor, in particular StemRegenin 1 (SR1) and in the presence of an immobilized Notch ligand.
(ii) The in vitro method as above, wherein the culture medium further contains TNF-alpha.
(iii) The in vitro method as above, wherein the antagonist of the Aryl hydrocarbon/Dioxin receptor, in particular SR1, is present, in the culture medium, from day 0 of the culture.
(iv) The in vitro method of any of above, wherein the CD34+ cells have been isolated from an adult donor, or from cord blood.
(v) The in vitro method of any of above, wherein the cells are cultured in presence of an antagonist of the Aryl hydrocarbon/Dioxin receptor, in particular SR1, for at most 10 days.
(vi) The in vitro method of any of above, wherein the cells are cultured in presence of the antagonist of the Aryl hydrocarbon/Dioxin receptor, in particular SR1, between 3 and 7 days.
(vii) The in vitro method of any of above, wherein the antagonist of the Aryl hydrocarbon/Dioxin receptor, in particular SR1, is added to the medium culture at a concentration between 1 ng/ml and 300 ng/ml and preferably higher or equal to 1 ng/ml, or higher or equal to 3 ng/ml, or higher or equal to 10 ng/ml, and preferably lower than 200 ng/ml, or 150 ng/ml and generally between 3 ng/ml and 100 ng/ml.
(viii) The in vitro method of any of above, wherein the Notch ligand is the soluble domain of the Delta-like-4 ligand, fused to a Fc region of an IgG protein, preferably an IgG2 protein.
(ix) The in vitro method of any of above, wherein the cells are also exposed to a fibronectin fragment, wherein said fragment comprises the RGDS and CS-1 patterns as well as a heparin-binding domain, preferably immobilized on the inner surface of the culture vessel.
(x) The in vitro method of above, wherein the fibronectin fragment is Retronectin®, as disclosed above.
(xi) The in vitro method of any of above, wherein the culture medium also contains a vector intended for transfection or transduction of the CD34+ cells, during at least some time of exposure of the CD34+ cells to the Notch ligand.
(xii) The in vitro method of any of above, wherein the culture medium contains at least three, and preferably all four, cytokines or growth factors chosen from the group consisting of Interleukin 7 (IL-7), SCF (Stem Cells Factor), thrombopoietin (TPO), and Flt3 ligand (FLT3L).
(xiii) An (in vitro) method for obtaining T cells progenitors, comprising the steps of
  a. performing the method according to any of above and
  b. purifying the generated T cells progenitors
  c. optionally conditioning the T cells progenitors in a pouch for injection to a patient.
(xiv) An in vitro method for obtaining transformed T-cells progenitors, comprising the steps of
  a. culturing CD34+ cells in a medium comprising an antagonist of the Aryl hydrocarbon/Dioxin receptor, in particular SR1, and in the presence of an immobilized Notch ligand
  b. exposing the cells to a vector intended for transfection or transduction of CD34+ cells.
(xv) An in vitro method for obtaining modified T-cells progenitors, comprising the steps of
  a. culturing CD34+ cells in a medium comprising an antagonist of the Aryl hydrocarbon/Dioxin receptor, in particular SR1, and in the presence of an immobilized Notch ligand b. exposing the cells to a vector or nucleic acid sequences containing the element appropriate for gene editing.

The invention also relates to a kit for performing any method as indicated above, comprising:
(i) a coating medium containing a ligand of Notch (in particular the soluble domain of the Delta-like-ligand, fused to a Fc region of an IgG protein, in particular a IgG2 protein), and optionally a fibronectin fragment
(ii) a medium adapted for culturing (and/or expanding) CD34+ cells and T cells such as α-MEM, DMEM, RPMI 1640, IMDM, BME, McCoy's 5A, StemSpan™ SFII (StemCell Technologies) media, X-VIVO™ medium or Fischer's medium
(iii) a progenitor expansion medium containing TNF-alpha and preferably three cytokines, in particular selected from SCF, TPO, Flt3L, and IL-7. It is preferred when the progenitor expansion medium contains TNF-alpha and all four cytokines SCF, TPO, Flt3L, and IL-7.

In another embodiment, the invention relates to a kit comprising the same elements (i) and (ii) as indicated above, and a progenitor expansion medium (iii) which contains an antagonist of the Aryl hydrocarbon/Dioxin receptor, in particular SR1, and preferably three cytokines, in particular selected from SCF, TPO, Flt3L, and IL-7. It is preferred when the progenitor expansion medium contains SR1 and all four cytokines SCF, TPO, Flt3L, and IL-7.

In another embodiment, the progenitor expansion medium (iii) contains TNF-alpha and an antagonist of the Aryl hydrocarbon/Dioxin receptor, in particular SR1, and preferably three cytokines, in particular selected from SCF, TPO, Flt3L, and IL-7. It is preferred when the progenitor expansion medium contains TNF-alpha, SR1 and all four cytokines SCF, TPO, Flt3L, and IL-7.

Such kit is particularly adapted and designed for performing the methods herein disclosed.

The coating medium (i) is first used to coat the walls of a culture vessel.

The medium (ii) is then used to culture CD34+ cells (either obtained from cord blood or from mobilized peripheral blood, in particular from an adult). Such medium is generally and preferably used at a 1× concentration (i.e. it can be used without dilution).

The medium (iii) is generally presented as a 10× dilution (i.e. it has to be diluted in a medium (ii) for use. The reconstituted medium from media (ii) and (iii) is then used to promoter differentiation of the CD34+ cells to T-cell progenitors, in the T-cell lineage, as disclosed above.

The invention also relates to a method for increasing the number of T cells in a subject in need thereof, the method comprising administering to the subject an effective number of progenitor T cells as obtained by a method disclosed herein.

The invention also relates to progenitor T cells as obtained by any method herein disclosed for their use for treating a subject in need of an increased number of T cells.

In particular, the subject is a human.

In particular, the administered progenitor T cells are autologous. In another embodiment, the administered progenitor T cells are allogeneic.

In particular, the subject in need of the increased number of T cells has a medical condition causing or resulting in lymphopenia, in particular cancer, HIV infection, partial thymectomy, autoimmune disease, and/or organ transplant.

EXAMPLES

Example 1—Material and Methods

Human Cells

Figure 1:
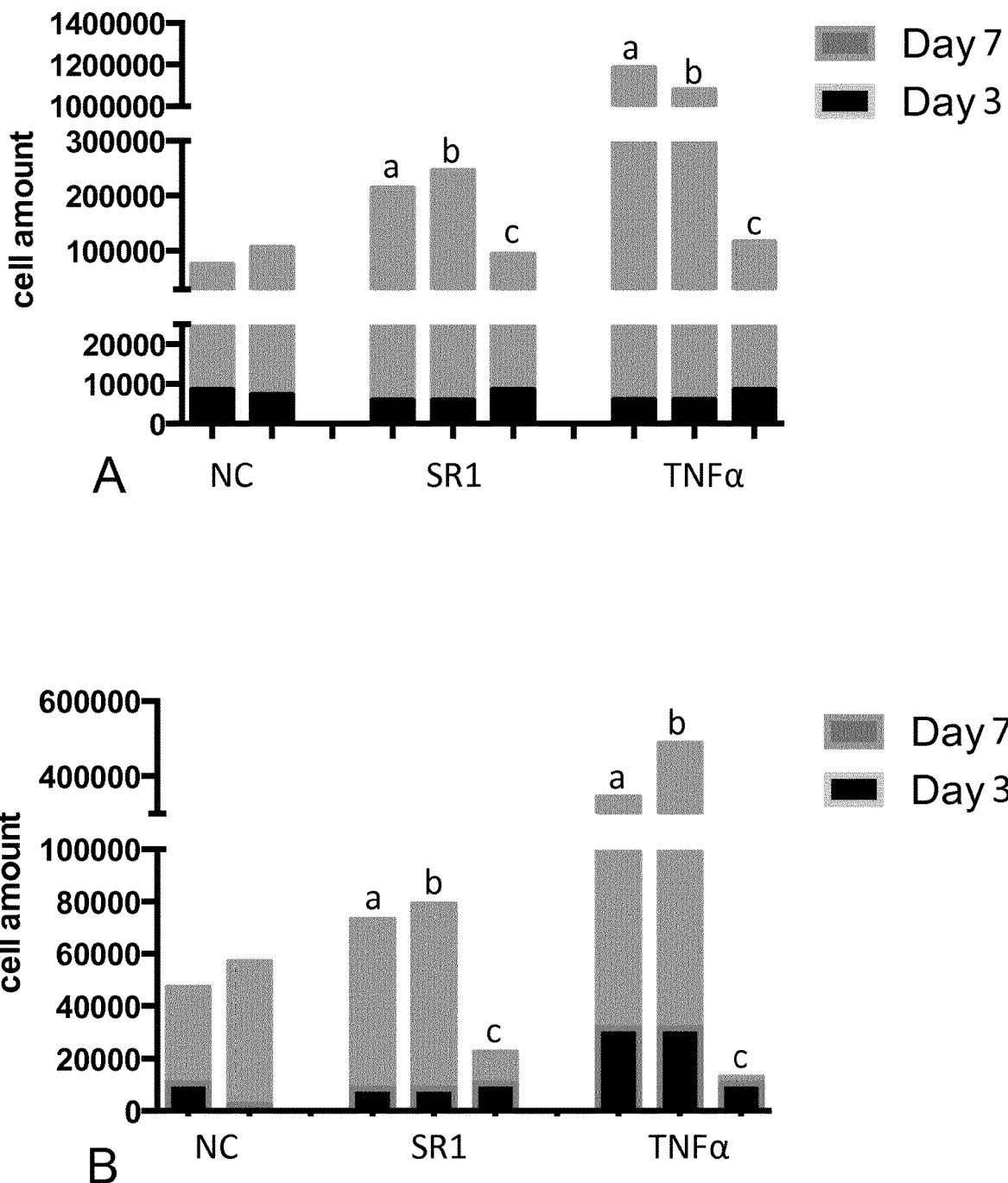
FIG. 1: Total nucleated cells number obtained starting with 20000 CD34+ cells from cord blood (CB, FIG. 1.A) or mobilized peripheral blood (mPB, FIG. 1.B), after 3 days (black bars) and 7 days (cumulative black and grey bars) of culture. NC: not complemented; SR1: addition of StemRegenin 1 (750 nM); TNF-alpha: addition of TNF-alpha (100 ng/ml); +(a), (b), (c): number of cells observed when the complements are added from 0-3 days of culture (a), 0-7 days of culture (b) or 4-7 days of culture (c).

Cord blood samples not eligible for banking were used for research purposes, following the provision of informed consent by the child's mother. Mobilized Peripheral Blood (mPB) samples were collected from healthy donors after G-CSF mobilization. Samples were directly enriched for CD34+ cells. The informed consent was given by each donor (Biotherapy Department, Necker Hospital, Paris).

Exposure of CD34+ Progenitor Cells to Notch Ligand DL-4

CD34+ cells from human CB or mobilized peripheral blood samples were cultured in 24-well plates or 6-well plates that had been coated with recombinant human fibronection (RetroNectin®, Clontech/Takara) and DL-4 (5 μg/ml, PX'Therapeutics, Grenoble, France). Coating was performed for 2 h at 37° C., DL-4 coated wells were then blocked with bovine serum albumin 2% (BSA) in phosphate-buffered saline (PBS) for 30 minutes at 37° C. and washed with PBS. Cultures were initiated at a concentration of $2 \times 10^4$ cells/well or $1 \times 10^5$ cells/well (for 24-well and 6-well plates respectively) in α-MEM medium (Gibco, life Technology), supplemented with NaHCO$_3$ (7.5%) (Gibco, life Technology) and 20% defined fetal calf serum (Hyclone, Thermo Fisher Scientific, Illkirch, France) and the recombinant human cytokines interleukin-7 (IL-7), Flt3-ligand (Flt-3), stem cell factor (SCF) and thrombopoietin (TPO) (all at 100 ng/ml and all purchased from PeproTech Inc, Rocky Hill, N.J.) with or without TNF-α (R&D Systems, US). After 3 days of culture, the cells were half replaced by fresh medium. Cultured cells were analyzed by fluorescence-activated cell sorting (FACS) after 3 and 7 days of culture on DL-4 respectively to exclude CD34-/CD7-myeloid cells from subsequent analyses.

In Vitro T Cell Differentiation Assay on OP9/DL1 Cells

The T-lymphoid potential of native CD34+ CB cells and TNF-α induced T cell progenitors generated by exposure to DL-4 was assessed in OP9/DL-1 co-cultures, as previously described (Six et al, Blood Cells Mol Dis. 2011 Jun. 15; 47(1):72-8 and Six J Exp Med. 2007 Dec. 24; 204(13):3085-93).

Quantitative, Real-Time Polymerase Chain Reactions Using RT2 Profiler Array

CD7+ cells were sorted on Ariall after 7 days of culture. Total RNA of sorted cell fractions from day 3 and day 7 was isolated with the Rneasy Micro Kit (Qiagen, Courtaboeuf, France). RT2 Profiler PCR arrays were performed following the protocol detailed in the RT2 Profiler PCR Array Handbook (SA Biosciences, Frederick Md.).

Flow Cytometry Analysis and Cell Sorting

Monoclonal antibodies against human CD34 (AC136), CD3 (BW264/56), CD45 (5B1) were purchased from Miltenyi Biotech (Bergisch Gladbach, Germany), and CD4 (SK4), CD7 (M-T701), CD25 (M-A251), 7-aminoactinomycin D (7AAD) were from BD Biosciences (San Jose, Calif.). Anti-human CD8 (RPAT8) was from Sony Biotechnology (San Jose, USA). The Anti-human Ctip2 (Bcl11b) antibody was from Abcam (Cambridge, UK).

Human cells were stained and analyzed using a Gallios analyzer (Beckman Coulter, Krefeld, Germany). Cells from xenogenic recipients were analysed on a MACSQuant® apparatus (Miltenyi Biotech, Bergisch Gladbach, Germany). The data were analyzed using FlowJo software (Treestar, Ashland, Oreg.) after gating on viable, 7AAD-negative cells. Cell subsets were sorted on an ARIA II system.

Cell Proliferation Assays

For cell proliferation assays, CD34+ cells from CB and mPB were labeled using the CellTrace™ CFSE kit (Life Technologies, Carlsbad, Calif.) prior to culture with DL-4 and TNF-alpha (Life Technologies). The cells' staining intensity was measured prior to culture each day from day 3 to day 7. CFSE-positive cell were analyzed on a Gallios cytometer (Beckman Coulter).

Cell Cycle Assays

For cell cycle analysis, cells were stained with Hoechst33342 (Life technology) and Ki67-PC5 (BD Bioscience) after fixed with Fixative reagent of PerFix-nc kit (Beckman Coulter) at room temperature for 15 min, and added permeablizing reagent. The data were analyzed using FlowJo software (version 10.2, Treestar, Ashland, Oreg.) after gating on viable, 7AAD-negative cells.

Adoptive Transfer of In Vitro-Generated T-Cell Progenitors Derived from Adult HSPCs into NSG Neonates All experiments and procedures with animals were performed in compliance with the French Ministry of Agriculture's regulations on animal experiments. The injection of in vitro generated human T-cell progenitors in NSG mice has been approved by the Ministry of Higher Education and Research (APAFIS 2101-2015090411495178v4).

The NSG (NOD-Scid(IL2Rg$^{null}$)) mice (obtained from the Jackson Laboratory, Bar Harbor, Me., http://www.jax.org) were kept in a pathogen-free facility. Progeny derived from mPB CD34+ HSPCs in 7-day DL-4 cultures with or without TNFα ($3 \times 10^5$ or $1 \times 10^6$) were injected intra-hepatically into NSG neonates (0-4 days old). Control mice were injected with either $3 \times 10^5$ non-cultured mPB CD34+ cells or 100 ul PBS.

Average engraftment levels of NSG mice were determined from 4 to 12 weeks post-transplant. Flow cytometry analysis was performed on freshly cells collected from femur, thymus, peripheral blood and spleen. Cells were treated with 1× red blood cell lysis buffer (Biolegend, US) and washed before stained by antibodies.

Analysis of T Cell Receptor Diversity

TCR gene rearrangement analysis was performed in duplicate and on the two independently purified subsets (average is shown).

TCR-δ quantification (D δ2-D δ3, D δ2-J δ1, and D δ3-J δ1) was performed with the listed sets of primers and probes.

The following were used for D δ2-D δ3 rearrangements:

D δ2,
(SEQ ID NO: 9)
5'-CAAGGAAAGGGAAAAAGGAAGAA-3';

D δ3,
(SEQ ID NO: 10)
5'-TTGCCCCTGCAGTTTTTGTAC-3';
and

D'3 probe,
(SEQ ID NO: 11)
5'-ATACGCACAGTGCTACAAAACCTACAGAGACCT-3'.

The following primers and probe were used for D δ2-J δ1 rearrangements:

D δ2,
(SEQ ID NO: 12)
5'-AGCGGGTGGTGATGGCAAAGT-3';

J δ1,
(SEQ ID NO: 13)
5'-TTAGATGGAGGATGCCTTAACCTTA-3';
and

J δ1 probe,
(SEQ ID NO: 14)
5'-CCCGTGTGACTGTGGAACCAAGTAAGTAACTC-3'

The following were used for D δ3-J δ1 rearrangements:

D δ3,
(SEQ ID NO: 15)
5'-GACTTGGAGAAAACATCTGGTTCTG-3';

J δ1 primer and J δ1 probe.

The analysis of TCR rearrangements by multiplex fluorescent PCR was performed by separation of fluorochrome-labeled single stand PCR products in a capillary sequencing polymer and detected via automated laser scanning.

Apoptosis Assays

Cells were washed by cold PBS and resuspended in binding buffer at a concentration of 1 million cells/ml. After adding 5 ul Annexin V-PE (BD Bioscience) and 2 ul 7AAD, cells were incubated in the dark at room temperature for 15 min. Subsequently, cells were washed with 500 ul binding buffer and resuspended in 100 ul binding buffer to be analyzed within 1 hour.

Figure 2:
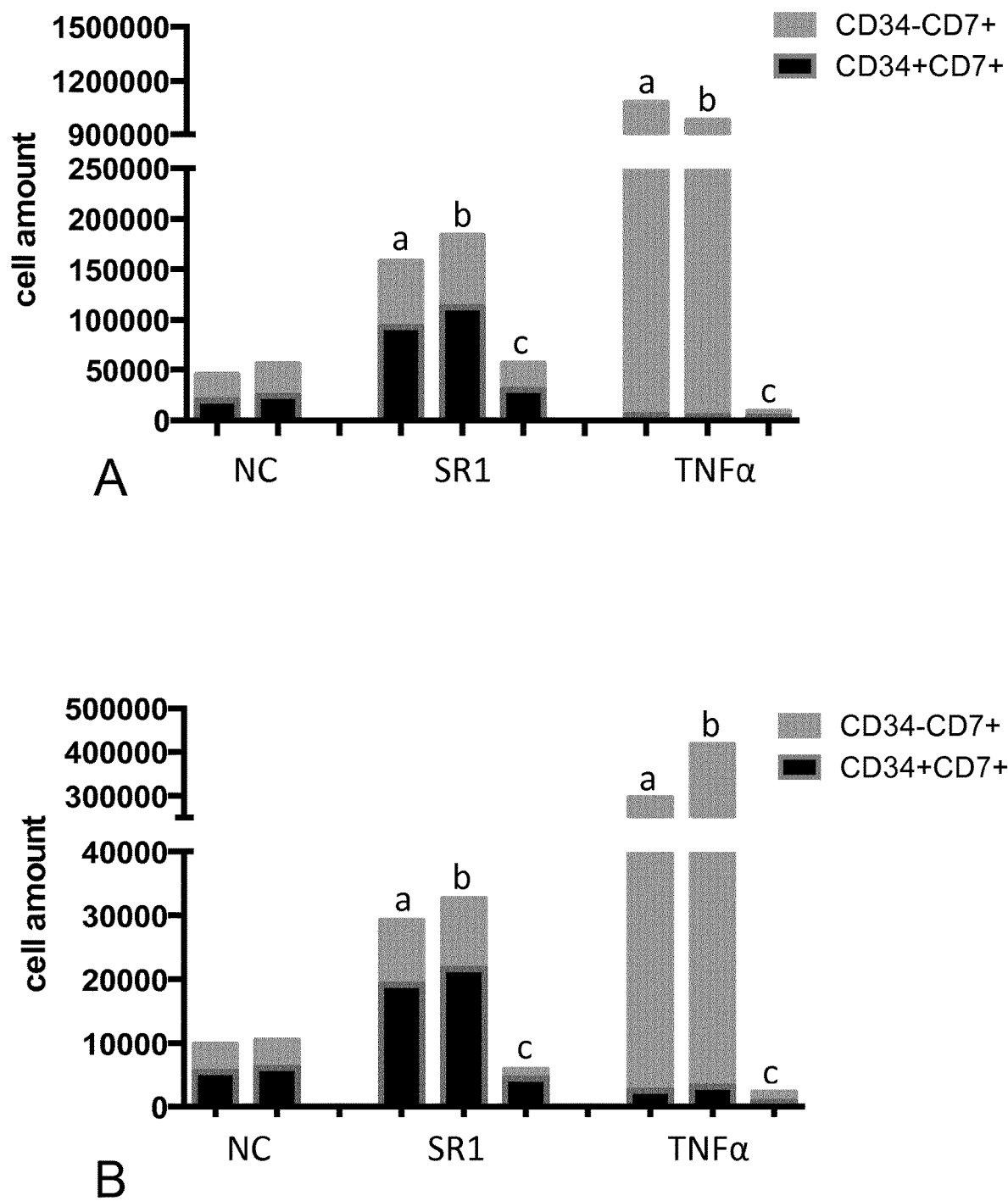
FIG. 2: Number of CD7+ T-cell precursors obtained at day 7 starting with 20000 CD34+ cells from cord blood (CB, FIG. 2.A) or mobilized peripheral blood (mPB, FIG. 2.B). Black bars: CD34+ CD7+ cells; grey bars: CD34-CD7+ cells. (a), (b), (c): number of cells observed when the complements are added from 0-3 days of culture (a), 0-7 days of culture (b) or 4-7 days of culture (c).

Example 2: Improvement on the Expansion and Differentiation of T-Cell Precursors When CD34+ cells are cultured with DL-4, FIG. 1 shows that addition of TNF-alpha to the cell culture medium makes it possible to multiply the total number of cells recovered at day 7 by 10 times as compared to culture without TNF-alpha, either when starting with CD34+ cells issued from cord blood (FIG. 1.A) or from PB (FIG. 1.B).
FIG. 2 shows that addition of TNF-alpha to the cell culture medium makes it possible to multiply the number of CD7+ cells in by 20 to 40 times, either when starting with CD34+ cells issued from cord blood (FIG. 2.A) or from PB (FIG. 2.B). The improvement is especially high for the CD34−CD7+ cell population.

Example 3: Analysis of the Surface Markers of the T Cell Progenitors

The surface markers present at the surface of the cells obtained after 7 days of culture were determined by flow cytometry.

|  | Cord blood | | | | mPB | | | |
| --- | --- | --- | --- | --- | --- | --- | --- | --- |
|  | CD34+ CD7+ | CD34− CD7+ | CD34+ CD7− | CD34− CD7− | CD34+ CD7+ | CD34− CD7+ | CD34+ CD7− | CD34− CD7− |
| −TNFα | 29.5 | 38.9 | 15.4 | 16.3 | 15.1 | 11.3 | 32.9 | 40.7 |
| +TNFα | 0.39 | 95.6 | 0.76 | 3.22 | 0.68 | 90.1 | 2.75 | 6.49 |

|  | Cord blood | | | | mPB | | | |
| --- | --- | --- | --- | --- | --- | --- | --- | --- |
|  | CD5+ CD7+ | CD5− CD7+ | CD5+ CD7− | CD5− CD7− | CD5+ CD7+ | CD5− CD7+ | CD5+ CD7− | CD5− CD7− |
| −TNFα | 1.56 | 66.8 | $5.10^{-3}$ | 31.6 | 0.069 | 26.4 | 0.027 | 73.5 |
| +TNFα | 0.66 | 95.4 | 0.012 | 3.97 | 3.01 | 87.7 | 0.24 | 9.00 |

These tables show that addition of TNF-alpha leads to an increase in the proportion of CD7+ cells, without really increasing the proportion of CD5+ cells.

After 7 day culture, HSPCs differentiate into CD34− CD7+ CD5− T-cell precursors.
The surface markers present at the surface of the cells obtained after 10 days of culture were also determined by flow cytometry.
No expression of CD1a was found (data not shown).
The kinetics of modification of the surface markers was studied and it was found that presence of TNF-alpha in the culture medium increases the proportion of CD7+ from day 4 up to day 7 (data not shown).

Example 4: Rearrangement of T Cell Receptors

DL-4 T-cell precursors do not exhibit any signs of TCR rearrangement with or without TNF-alpha or SR1 after 7 days of culture (data not shown).

Specific analysis of rearrangement was performed:
Results of TCRdelta Rearrangements
Detection of D52-D53 rearrangements in CB-NC et CB-SR1. No other TCRdelta rearrangements were detected.
Results were in accordance with RQ-PCR quantification
Results of TCRgamma Rearrangements
No TCRgamma rearrangements were detected.
Results of TCRbeta Rearrangements
No TCRbeta rearrangements were detected.

Example 5: T-Commitment of TNFα Induced T-Cell Precursors

Figure 3:
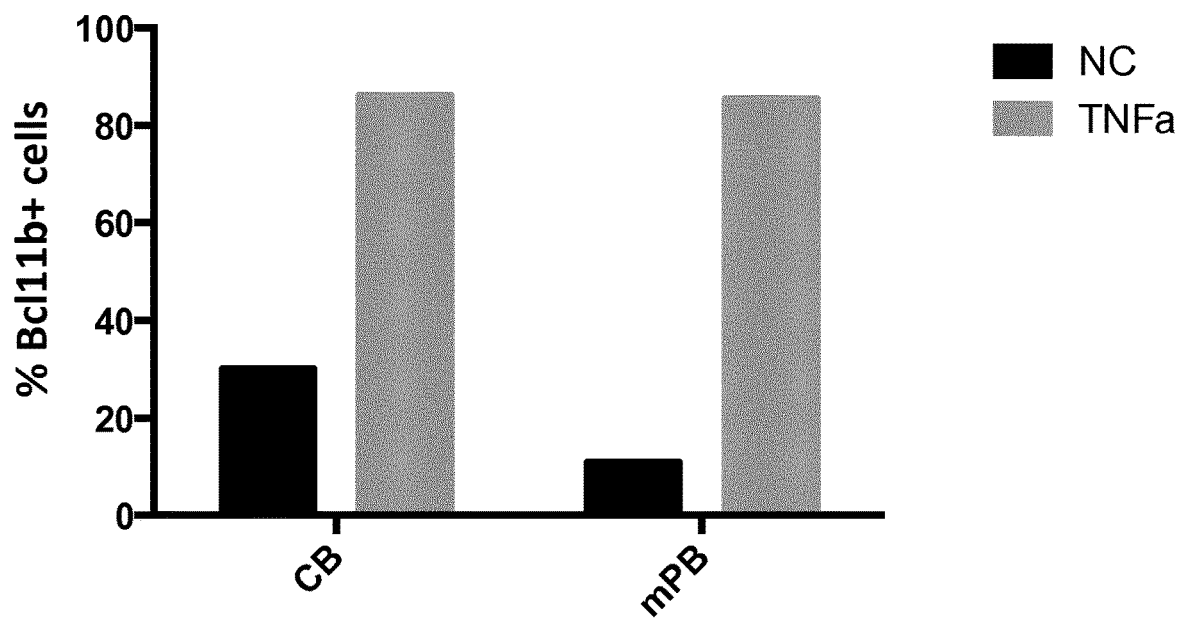
FIG. 3: Expression of Bcl11b was analyzed on lived cells after 7 days of culture obtained starting with CD34+ cells from cord blood (CB) or mobilized peripheral blood (mPB) cultured in the presence (grey bars) or absence (black bars) of TNF-alpha.

Bcl11b is an important transcriptional factor uniquely switched on since T-cell commitment and absolutely required for T-cell differentiation.
Intracellular staining on T-cell precursors cultured with TNF-alpha showed positive expression of Bcl11b for both CD34+ cells issued from cord blood, and mPB. FIG. 3 shows that TNF-alpha increases the proportion of total cells expressing Bcl11b transcription factor. When cultured with TNF-alpha, the proportion of Bcl11b expressing cells was increased.

Example 6: Differentiation on Other Lineages

Presence of other cell surface markers (CD14 and CD33) specific of other lineages was assessed.

Figure 5:
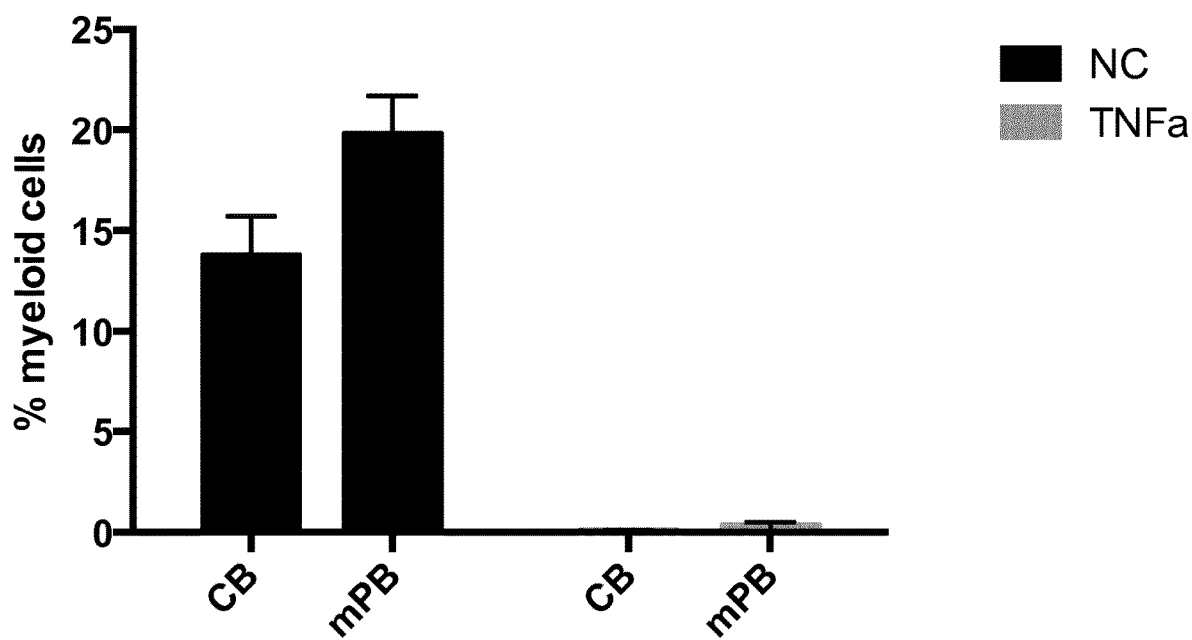
FIG. 5: Frequency of myeloid cells at day 7 obtained starting from CD34+ cells from cord blood (CB) or mobilized peripheral blood (mPB) in presence (grey bars) or not (black bars) of TNF-alpha (Mean±SEM).

FIG. 5 shows that the culture in the presence of TNF-alpha made such cells not detectable, whereas their proportion is less than 22% when CD34+ cells are cultured without TNF-alpha.

Example 7: TNF-Alpha Reduces Apoptosis of the Cells

Apoptosis markers (7AAD and Annexin5) were studied.

| 7AAD +/− AnnexinV+ apoptotic cells (%) | CB | mPB |
| --- | --- | --- |
| −TNFα | 1.66 | 10.56 |
| +TNFα | 0.28 | 0.96 |

This table shows that culture in presence of TNF-alpha reduces the presence of the apoptosis markers. This is particularly apparent for mPB.

Example 8: Dose Response Assay of TNF-Alpha

Various doses of TNF-alpha were used.

Figure 6:
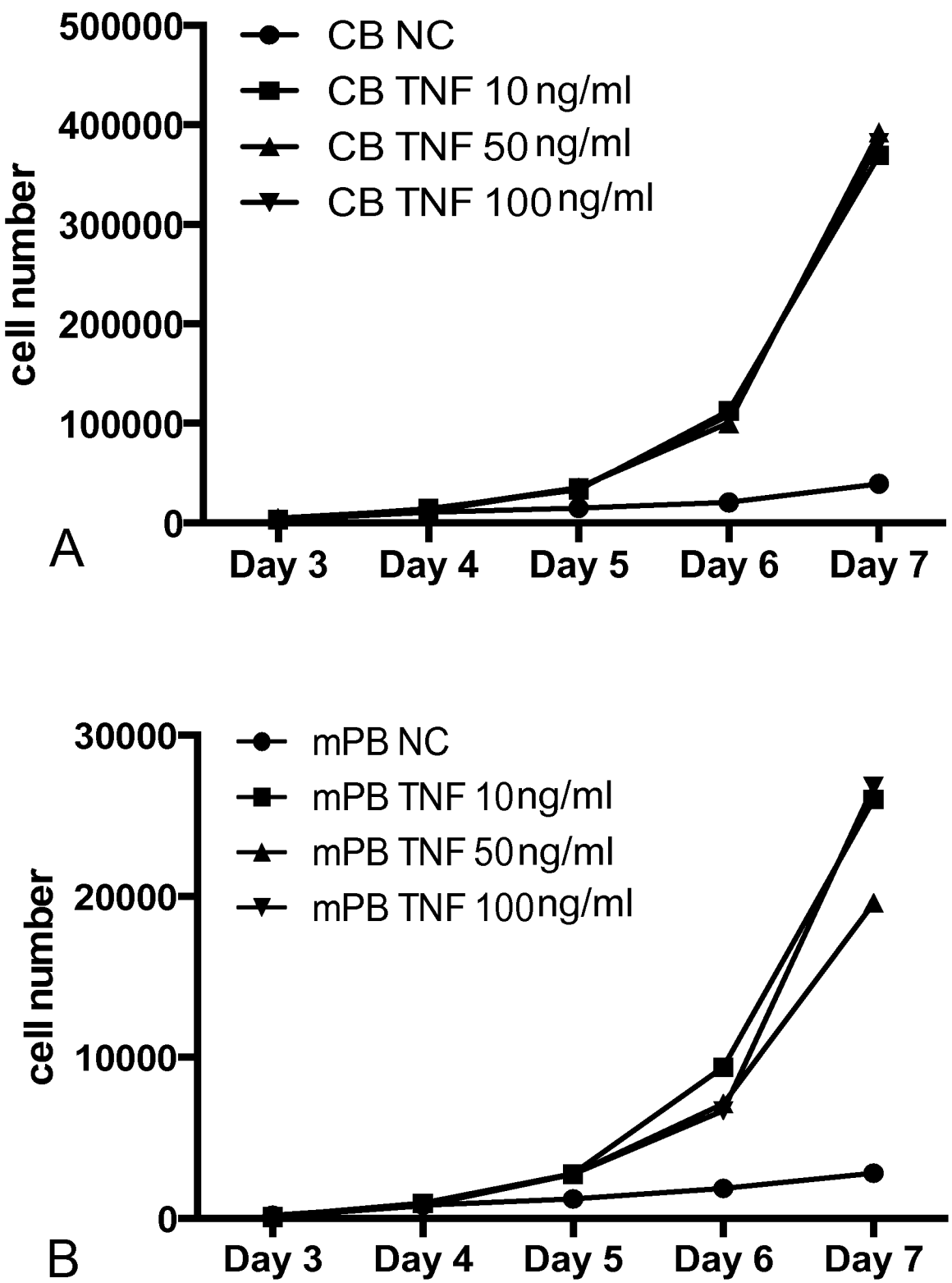
FIG. 6: Total CD7+ cells number obtained from day 3 to day 7 in a dose response assay of TNF-alpha, starting with CD34+ cells from cord blood (CB, FIG. 6.A) or mobilized peripheral blood (mPB, FIG. 6.B).

FIG. 6 shows that TNFa may increase CD7+ cell numbers during culture, when the concentration is more than 10 ng/ml, either for CB cells (FIG. 6.A) or mPB cells (FIG. 6.B).

Kinetics of the dose response showed that TNF-alpha increases the T-cell differentiation after only 4 days of culture in DL-4. There was no difference between the concentration 10, 50 and 100 ng/ml (not shown).

To determine the threshold of effective concentration, analysis of lower concentrations (0.01-10 ng/ml) was performed.

Figure 7:
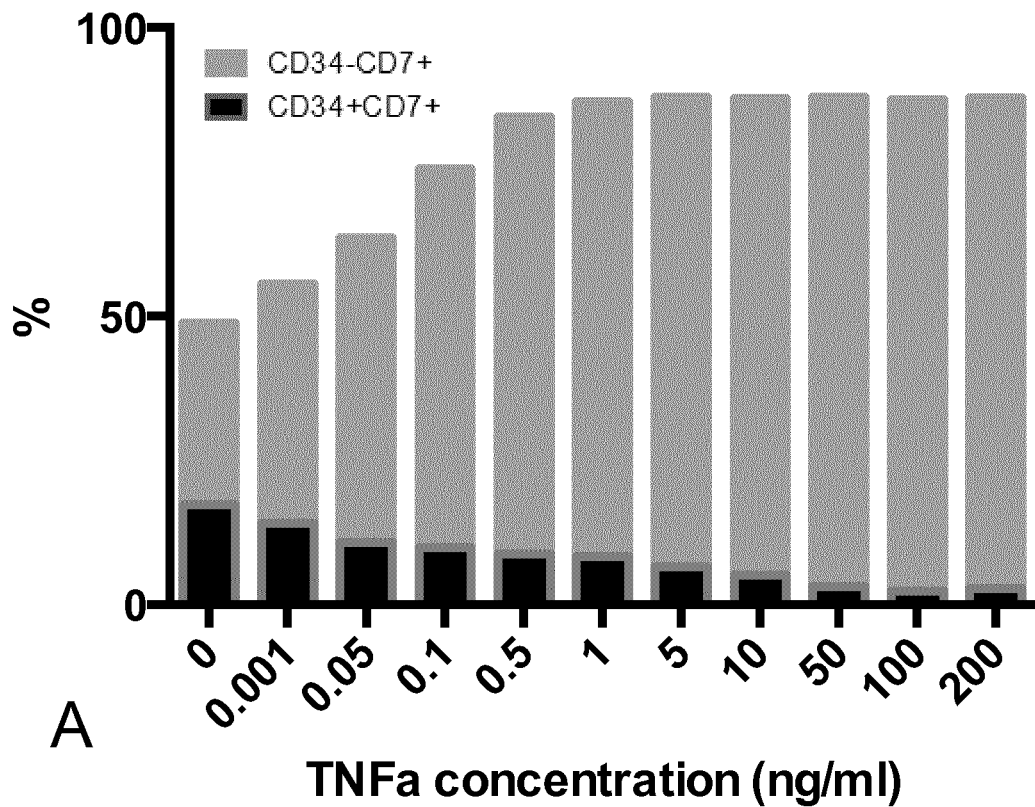
FIG. 7: Proportion of CD34-CD7+ cells (grey bars) vs CD34+ CD7+ cells (black bars) in a dose response assay of TNF-alpha starting with CD34+ cells from cord blood (CB, FIG. 7.A) or mobilized peripheral blood (mPB, FIG. 7.B)
Figure 7:
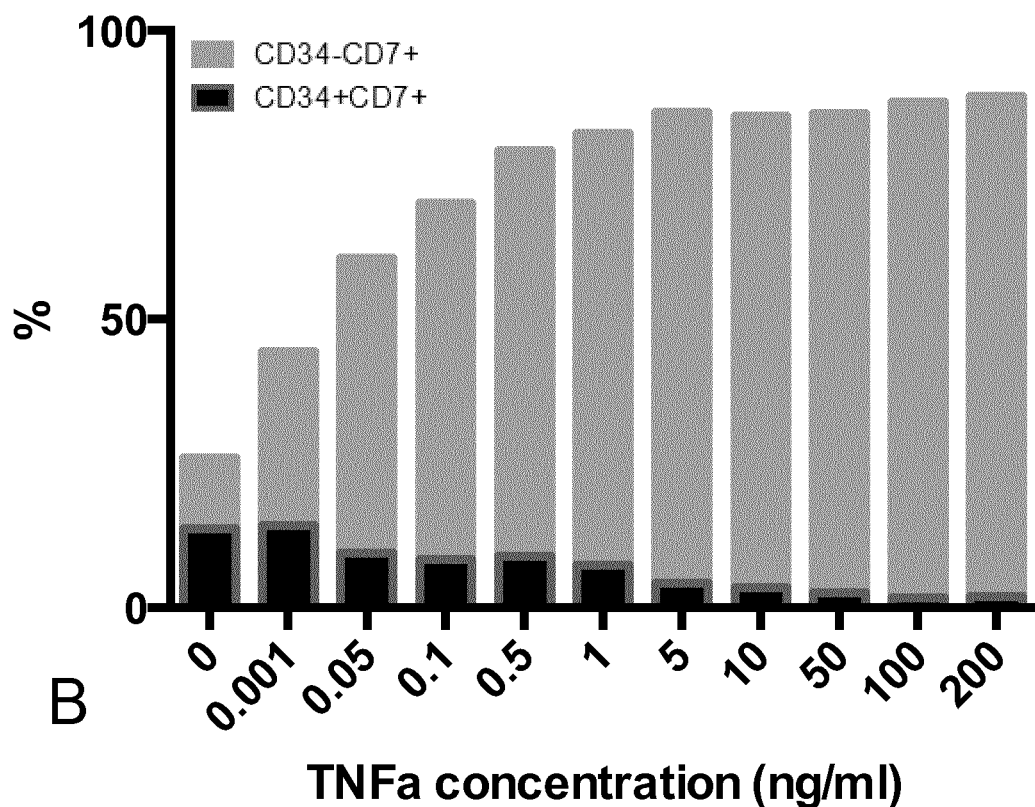

The effect of TNF-alpha on CB and mPB on T-cell differentiation (percentage of CD34– CD7+ cells) was found to be concentration-dependent at low concentration (FIG. 7). The total number of CD7+ T-cell precursors was not different from 5 ng/ml to 100 ng/ml.

Example 9: Proliferation Analysis During Culture

TNF-alpha was found to increase the proliferation of CD34+ CD7+ T-cell precursors since day 3 in DL-4 culture as compared to culture conditions without TNF-alpha (data not shown).

Example 10: Synergy Between TNF-Alpha and the Notch Ligand

Figure 4:
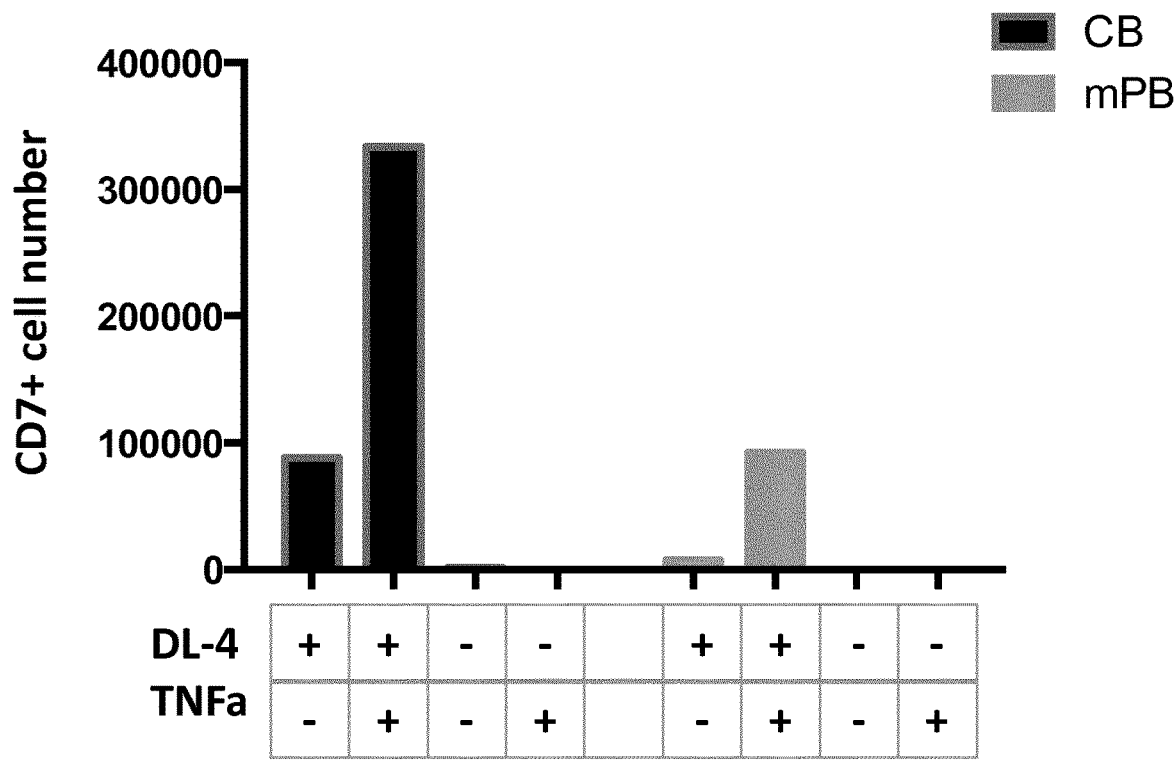
FIG. 4: Combined effect of TNF-alpha and the Notch ligand DL4 on the number of CD7+ cells obtained at day 7 starting from CD34+ cord blood cells (CB, black bars, left) or mobilized peripheral blood (mPB, grey bars, right). (+/− means presence or absence of DL4 or TNF-alpha).

FIG. 4 shows that without DL4, both CB and mPB failed to differentiate into CD7+ T-cell precursors. Even the complementation of the medium with TNF-alpha couldn't rescue it.

When both TNF-alpha and the Notch ligand are present, the effect observed is very high. It thus seems that there is a synergy between these two compounds and that the effect of TNF-alpha on T-cell differentiation is likely Notch dependant.

Example 11: Addition of TNF-Alpha Increases Proliferation of CD7+ Progenitors After 7 days of culture in presence of TNF-alpha, CD34+ CD7–, CD34+ CD7+ and CD34–CD7+ subsets were sorted, stained with CFSE (Carboxyfluorescein succinimidyl ester) and the dilution of CFSE (surrogate marker of cell proliferation) was followed from day 8 to 10.

Only CD34+ CD7+ and CD34–CD7+ cells show increased proliferation when cultured with TNF-alpha. (Data not shown)

Example 12: Cell Cycle Analysis

Figure 8:
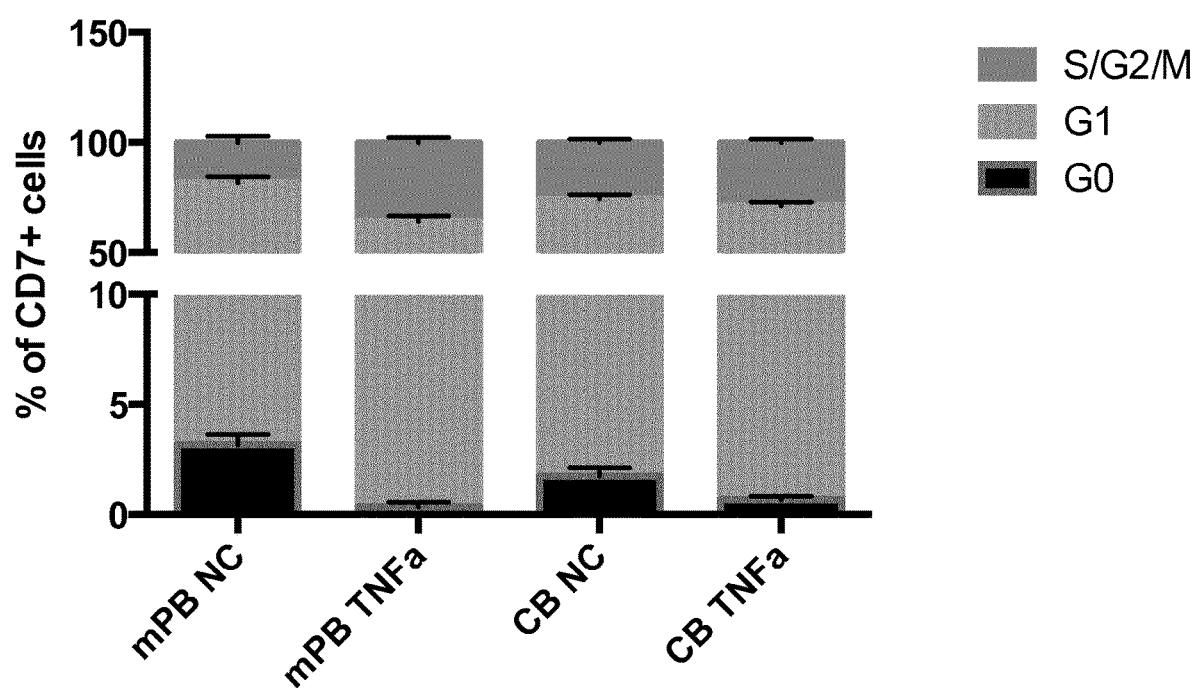
FIG. 8: Proportion of cells in the different phases of the cellular cycle. A. CB: cells differentiated from cord blood; B. cells differentiated from mobilized peripheral blood cells. NC: non complemented; TNF-alpha: cultured in presence of TNF-alpha (20 ng/ml); SR1: cultures in presence of SR1 (30 ng/ml)

Analysis of the cell cycle was performed. It was observed that more cells were released from G0 phase in presence of TNF-alpha on both CB and mPB derived CD7+ progenitors (FIG. 8).

Example 13: Combination of SR1 and TNFa

Figure 9:
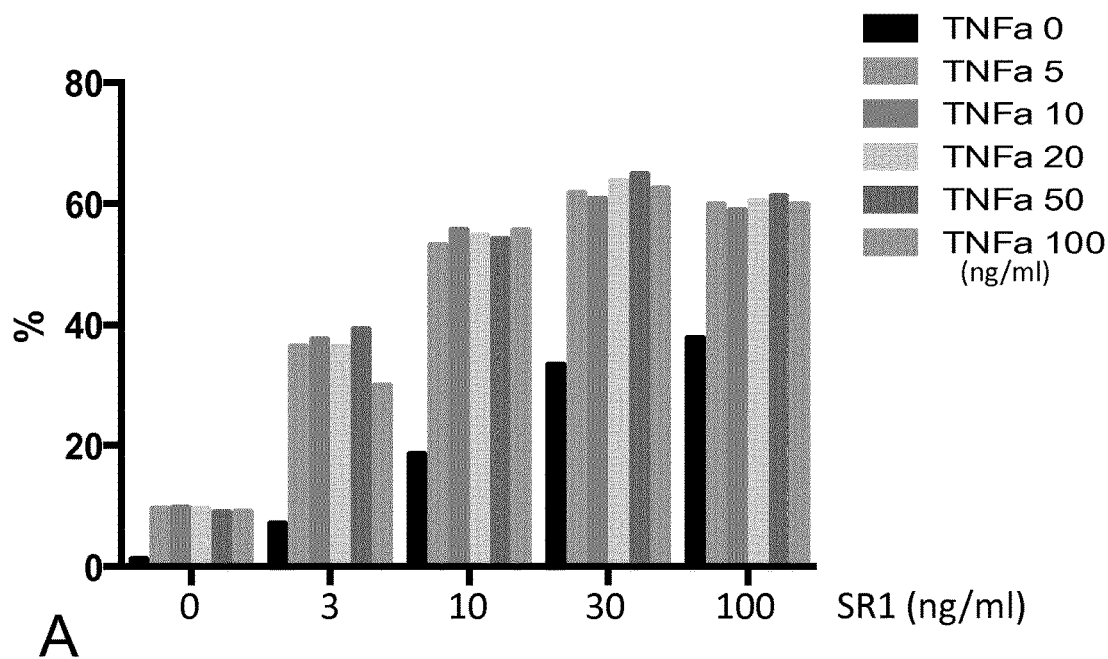
FIG. 9: percentage (A) and total number (B) of CD5+ CD7+ cells cultured starting with CD34+ cells from cord blood in presence of TNF-alpha and/or SR1 at various concentrations, after 7 days of culture.
Figure 9:
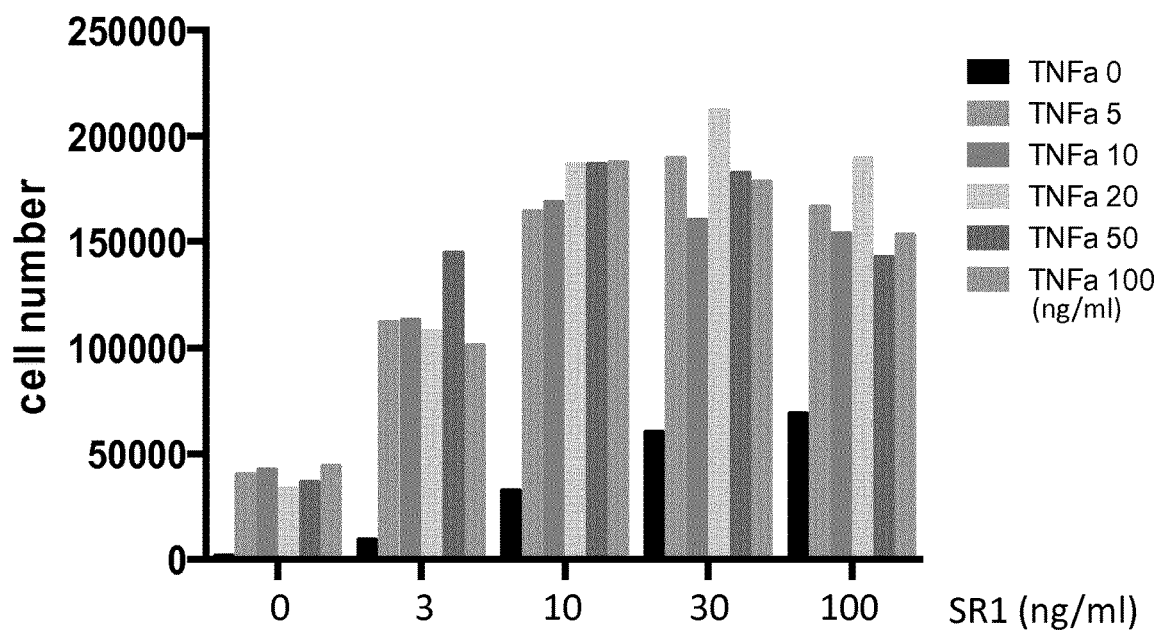

SR1 accelerates T-cell differentiation as shown by the presence of CD5+CD7+ cells at day 7. The number of CD5+CD7+ cells is increased by the presence of both TNF-alpha and SR1 (FIG. 9).

Example 14: In Vivo Data

T-cell precursors induced in presence of TNF-alpha may largely fasten the reconstitution of the T-lineage in vivo.

Indeed, 4 weeks post-transplantation, recipient mice injected with mPB T-cell precursors produced in the presence of TNF-alpha have larger thymus than mice injected with mPB T-cell precursors produced without TNF-alpha. T-cell precursors induced in presence of TNF-alpha can differentiate to activated TCR$\alpha\beta$ T cells within 4 weeks in vivo. (Data not shown)

In summary, addition of TNF-alpha from day 0 in the DL-4 culture system leads to an increase of T-cell progenitors (defined by the surface expression of CD7) of 40 fold for mPB HSPC and 20 fold for CB HSPC at day 7.

The CD7+ T-cell progenitors generated from both CB and mPB were mostly CD34– and were CD1a negative. Cells were also mostly CD5 negative.

They expressed Bcl11b, which is important fine-turning molecular for T-commitment and further T-cell differentiation.

They did not exhibit any signs of T-cell receptor rearrangements.

Their phenotype and molecular characteristics were similar to the one of the CD34–CD7+ T-cell progenitors obtained without TNF-alpha.

Regarding the mechanisms involved in TNF-alpha action, TNF-alpha decreases expression of apoptosis markers and increases cell proliferation during the culture. It also inhibits myeloid cell production.

The use of TNF-alpha in the DL4 culture system increase to a huge extent the amounts of T-cell progenitors produced from both human adult and cord blood HSPC. It may thus overcome the difficulty to obtain large amounts of T-cell progenitors from adult HSPC. It may also decrease the number of starting HSPC required in future clinical trials and the quantity of GMP grade and other reagents required, thus decreasing the costs of production of these T-cell progenitors.

The invention claimed is:

1. An isolated T cell progenitor population comprising CD7+ T cell progenitors,
    wherein said CD7+ T cell progenitors comprise CD34− CD7+ T cell progenitors, wherein more than 80% of the CD7+ T cell progenitors are CD34−CD7+ T cell progenitors,
    wherein said CD34−CD7+ T cell progenitors comprise T cell progenitors with the following phenotype: CD7+ CD34−CD1a−CD5−,
    wherein said T cell progenitor population was prepared by culturing CD34+ cells in a culture medium comprising fetal serum, TNF-alpha, IL-7, thrombopoietin (TPO), Flt3L, and Stem cell factor (SCF), in the presence of an immobilized Delta-like-4 ligand and a fibronectin fragment for a period ranging from 5 to 7 days, wherein said fibronectin fragment comprises the RGDS (SEQ ID NO: 3) and connecting segment 1 (CS-1) patterns as well as a heparin-binding domain, wherein TNF-alpha is present in the culture medium at a concentration of at least 10 ng/mL,
    wherein fetal serum is present in the culture medium at a concentration of at least 15%, and
    wherein the culture medium does not comprise IL 3.

2. The isolated T cell progenitor population according to claim 1, wherein the CD7+CD34− cells are genetically modified by the introduction of a vector, wherein the vector encodes a Chimeric Antigen Receptor (CAR).

3. The isolated T cell progenitor population of claim 1, wherein the CD34+ cells are isolated from a human.

4. The isolated T cell progenitor population of claim 1, wherein the CD34+ cells are isolated from an adult donor.

5. The isolated T cell progenitor population of claim 1, wherein more than 80% of the CD7+ T cell progenitors are CD7+CD34−CD5−, CD7+CD34−CD1a−, or CD7+CD34−CD1a−CD5−.

* * * * *

SEQUENCE LISTING

```
<160> NUMBER OF SEQ ID NOS: 15

<210> SEQ ID NO 1
<211> LENGTH: 723
<212> TYPE: PRT
<213> ORGANISM: Artificial Sequence
<220> FEATURE:
<223> OTHER INFORMATION: Human Delta -1 (soluble fraction: 1-536) G502
      may be R

<400> SEQUENCE: 1

Met Gly Ser Arg Cys Ala Leu Ala Leu Ala Val Leu Ser Ala Leu Leu
```

```
  1               5                  10                 15
Cys Gln Val Trp Ser Ser Gly Val Phe Glu Leu Lys Leu Gln Glu Phe
                 20                 25                 30
Val Asn Lys Lys Gly Leu Leu Gly Asn Arg Asn Cys Cys Arg Gly Gly
                 35                 40                 45
Ala Gly Pro Pro Pro Cys Ala Cys Arg Thr Phe Phe Arg Val Cys Leu
 50                 55                 60
Lys His Tyr Gln Ala Ser Val Ser Pro Glu Pro Pro Cys Thr Tyr Gly
 65                 70                 75                 80
Ser Ala Val Thr Pro Val Leu Gly Val Asp Ser Phe Ser Leu Pro Asp
                 85                 90                 95
Gly Gly Gly Ala Asp Ser Ala Phe Ser Asn Pro Ile Arg Phe Pro Phe
                 100                105                110
Gly Phe Thr Trp Pro Gly Thr Phe Ser Leu Ile Ile Glu Ala Leu His
                 115                120                125
Thr Asp Ser Pro Asp Asp Leu Ala Thr Glu Asn Pro Glu Arg Leu Ile
                 130                135                140
Ser Arg Leu Ala Thr Gln Arg His Leu Thr Val Gly Glu Glu Trp Ser
145                150                155                160
Gln Asp Leu His Ser Ser Gly Arg Thr Asp Leu Lys Tyr Ser Tyr Arg
                 165                170                175
Phe Val Cys Asp Glu His Tyr Tyr Gly Glu Gly Cys Ser Val Phe Cys
                 180                185                190
Arg Pro Arg Asp Asp Ala Phe Gly His Phe Thr Cys Gly Glu Arg Gly
                 195                200                205
Glu Lys Val Cys Asn Pro Gly Trp Lys Gly Pro Tyr Cys Thr Glu Pro
210                215                220
Ile Cys Leu Pro Gly Cys Asp Glu Gln His Gly Phe Cys Asp Lys Pro
225                230                235                240
Gly Glu Cys Lys Cys Arg Val Gly Trp Gln Gly Arg Tyr Cys Asp Glu
                 245                250                255
Cys Ile Arg Tyr Pro Gly Cys Leu His Gly Thr Cys Gln Gln Pro Trp
                 260                265                270
Gln Cys Asn Cys Gln Glu Gly Trp Gly Gly Leu Phe Cys Asn Gln Asp
                 275                280                285
Leu Asn Tyr Cys Thr His His Lys Pro Cys Lys Asn Gly Ala Thr Cys
                 290                295                300
Thr Asn Thr Gly Gln Gly Ser Tyr Thr Cys Ser Cys Arg Pro Gly Tyr
305                310                315                320
Thr Gly Ala Thr Cys Glu Leu Gly Ile Asp Glu Cys Asp Pro Ser Pro
                 325                330                335
Cys Lys Asn Gly Gly Ser Cys Thr Asp Leu Glu Asn Ser Tyr Ser Cys
                 340                345                350
Thr Cys Pro Pro Gly Phe Tyr Gly Lys Ile Cys Glu Leu Ser Ala Met
                 355                360                365
Thr Cys Ala Asp Gly Pro Cys Phe Asn Gly Gly Arg Cys Ser Asp Ser
                 370                375                380
Pro Asp Gly Gly Tyr Ser Cys Arg Cys Pro Val Gly Tyr Ser Gly Phe
385                390                395                400
Asn Cys Glu Lys Lys Ile Asp Tyr Cys Ser Ser Ser Pro Cys Ser Asn
                 405                410                415
Gly Ala Lys Cys Val Asp Leu Gly Asp Ala Tyr Leu Cys Arg Cys Gln
                 420                425                430
```

```
Ala Gly Phe Ser Gly Arg His Cys Asp Asp Asn Val Asp Asp Cys Ala
        435                 440                 445
Ser Ser Pro Cys Ala Asn Gly Gly Thr Cys Arg Asp Gly Val Asn Asp
    450                 455                 460
Phe Ser Cys Thr Cys Pro Pro Gly Tyr Thr Gly Arg Asn Cys Ser Ala
465                 470                 475                 480
Pro Val Ser Arg Cys Glu His Ala Pro Cys His Asn Gly Ala Thr Cys
                485                 490                 495
His Glu Arg Gly His Gly Tyr Val Cys Glu Cys Ala Arg Gly Tyr Gly
            500                 505                 510
Gly Pro Asn Cys Gln Phe Leu Leu Pro Glu Leu Pro Pro Gly Pro Ala
        515                 520                 525
Val Val Asp Leu Thr Glu Lys Leu Glu Gly Gln Gly Gly Pro Phe Pro
    530                 535                 540
Trp Val Ala Val Cys Ala Gly Val Ile Leu Val Leu Met Leu Leu Leu
545                 550                 555                 560
Gly Cys Ala Ala Val Val Val Cys Val Arg Leu Arg Leu Gln Lys His
                565                 570                 575
Arg Pro Pro Ala Asp Pro Cys Arg Gly Glu Thr Glu Thr Met Asn Asn
            580                 585                 590
Leu Ala Asn Cys Gln Arg Glu Lys Asp Ile Ser Val Ser Ile Ile Gly
        595                 600                 605
Ala Thr Gln Ile Lys Asn Thr Asn Lys Lys Ala Asp Phe His Gly Asp
    610                 615                 620
His Ser Ala Asp Lys Asn Gly Phe Lys Ala Arg Tyr Pro Ala Val Asp
625                 630                 635                 640
Tyr Asn Leu Val Gln Asp Leu Lys Gly Asp Asp Thr Ala Val Arg Asp
                645                 650                 655
Ala His Ser Lys Arg Asp Thr Lys Cys Gln Pro Gln Gly Ser Ser Gly
            660                 665                 670
Glu Glu Lys Gly Thr Pro Thr Thr Leu Arg Gly Gly Glu Ala Ser Glu
        675                 680                 685
Arg Lys Arg Pro Asp Ser Gly Cys Ser Thr Ser Lys Asp Thr Lys Tyr
    690                 695                 700
Gln Ser Val Tyr Val Ile Ser Glu Glu Lys Asp Glu Cys Val Ile Ala
705                 710                 715                 720
Thr Glu Val

<210> SEQ ID NO 2
<211> LENGTH: 724
<212> TYPE: PRT
<213> ORGANISM: Artificial Sequence
<220> FEATURE:
<223> OTHER INFORMATION: Human delta-4 protein (soluble fraction 1-526)

<400> SEQUENCE: 2

Met Ala Ala Ala Ser Arg Ser Ala Ser Gly Trp Ala Leu Leu Leu Leu
1               5                   10                  15
Val Ala Leu Trp Gln Gln Arg Ala Ala Gly Ser Gly Val Phe Gln Leu
            20                  25                  30
Gln Leu Gln Glu Phe Ile Asn Glu Arg Gly Val Leu Ala Ser Gly Arg
        35                  40                  45
Pro Cys Glu Pro Gly Cys Arg Thr Phe Phe Arg Val Cys Leu Lys His
    50                  55                  60
```

```
Phe Gln Ala Val Val Ser Pro Gly Pro Cys Thr Phe Gly Thr Val Ser
 65                  70                  75                  80

Thr Pro Val Leu Gly Thr Asn Ser Phe Ala Val Arg Asp Asp Ser Ser
                 85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
```

```
                    485                 490                 495

Thr Asp Leu Ser Thr Asp Thr Phe Val Cys Asn Cys Pro Tyr Gly Phe
                500                 505                 510

Val Gly Ser Arg Cys Glu Phe Pro Val Gly Leu Pro Pro Ser Phe Pro
            515                 520                 525

Trp Val Ala Val Ser Leu Gly Val Gly Leu Ala Val Leu Leu Val Leu
        530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
                610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val Thr Pro Arg
        675                 680                 685

Leu Asp Leu Pro Ser Ala Leu Phe Thr Leu His Pro Gly Trp Asp Val
        690                 695                 700

Phe His Met Gln Arg Ala Ala Leu Arg Arg Arg Glu Trp Gln Glu
705                 710                 715                 720

Pro Asp Arg Leu

<210> SEQ ID NO 3
<211> LENGTH: 4
<212> TYPE: PRT
<213> ORGANISM: Artificial Sequence
<220> FEATURE:
<223> OTHER INFORMATION: RGDS pattern

<400> SEQUENCE: 3

Arg Gly Asp Ser
1

<210> SEQ ID NO 4
<211> LENGTH: 6
<212> TYPE: PRT
<213> ORGANISM: Artificial Sequence
<220> FEATURE:
<223> OTHER INFORMATION: heparin binding domain XBBXBX; B = basic amino
      acid; X = hydropathic amino acid
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

<400> SEQUENCE: 4

Xaa Asx Asx Xaa Asx Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: heparin binding domain XBBBXXBX; B = basic
      amino acid; X = hydropathic amino acid
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 5

Xaa Asx Asx Asx Xaa Xaa Asx Xaa
1               5

<210> SEQ ID NO 6
<211> LENGTH: 25
<212> TYPE: PRT
<213> ORGANISM: Artificial Sequence
<220> FEATURE:
<223> OTHER INFORMATION: CS-1 pattern

<400> SEQUENCE: 6

Asp Glu Leu Pro Gln Leu Val Thr Leu Pro His Pro Asn Leu His Gly
1               5                   10                  15

Pro Glu Ile Leu Asp Val Pro Ser Thr
            20                  25

<210> SEQ ID NO 7
<211> LENGTH: 754
<212> TYPE: PRT
<213> ORGANISM: Artificial Sequence
<220> FEATURE:
<223> OTHER INFORMATION: fusion protein human delta 4 - Fc receptor

<400> SEQUENCE: 7

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

-continued

```
Gly Thr Phe Ser Leu Ile Ile Glu Ala Trp His Ala Pro Gly Asp Asp
            115                 120                 125
Leu Arg Pro Glu Ala Leu Pro Pro Asp Ala Leu Ile Ser Lys Ile Ala
130                 135                 140
Ile Gln Gly Ser Leu Ala Val Gly Gln Asn Trp Leu Leu Asp Glu Gln
145                 150                 155                 160
Thr Ser Thr Leu Thr Arg Leu Arg Tyr Ser Tyr Arg Val Ile Cys Ser
                165                 170                 175
Asp Asn Tyr Tyr Gly Asp Asn Cys Ser Arg Leu Cys Lys Lys Arg Asn
            180                 185                 190
Asp His Phe Gly His Tyr Val Cys Gln Pro Asp Gly Asn Leu Ser Cys
            195                 200                 205
Leu Pro Gly Trp Thr Gly Glu Tyr Cys Gln Gln Pro Ile Cys Leu Ser
210                 215                 220
Gly Cys His Glu Gln Asn Gly Tyr Cys Ser Lys Pro Ala Glu Cys Leu
225                 230                 235                 240
Cys Arg Pro Gly Trp Gln Gly Arg Leu Cys Asn Glu Cys Ile Pro His
                245                 250                 255
Asn Gly Cys Arg His Gly Thr Cys Ser Thr Pro Trp Gln Cys Thr Cys
            260                 265                 270
Asp Glu Gly Trp Gly Gly Leu Phe Cys Asp Gln Asp Leu Asn Tyr Cys
            275                 280                 285
Thr His His Ser Pro Cys Lys Asn Gly Ala Thr Cys Ser Asn Ser Gly
            290                 295                 300
Gln Arg Ser Tyr Thr Cys Thr Cys Arg Pro Gly Tyr Thr Gly Val Asp
305                 310                 315                 320
Cys Glu Leu Glu Leu Ser Glu Cys Asp Ser Asn Pro Cys Arg Asn Gly
                325                 330                 335
Gly Ser Cys Lys Asp Gln Glu Asp Gly Tyr His Cys Leu Cys Pro Pro
            340                 345                 350
Gly Tyr Tyr Gly Leu His Cys Glu His Ser Thr Leu Ser Cys Ala Asp
            355                 360                 365
Ser Pro Cys Phe Asn Gly Gly Ser Cys Arg Glu Arg Asn Gln Gly Ala
370                 375                 380
Asn Tyr Ala Cys Glu Cys Pro Pro Asn Phe Thr Gly Ser Asn Cys Glu
385                 390                 395                 400
Lys Lys Val Asp Arg Cys Thr Ser Asn Pro Cys Ala Asn Gly Gly Gln
                405                 410                 415
Cys Leu Asn Arg Gly Pro Ser Arg Met Cys Arg Cys Arg Pro Gly Phe
            420                 425                 430
Thr Gly Thr Tyr Cys Glu Leu His Val Ser Asp Cys Ala Arg Asn Pro
            435                 440                 445
Cys Ala His Gly Gly Thr Cys His Asp Leu Glu Asn Gly Leu Met Cys
450                 455                 460
Thr Cys Pro Ala Gly Phe Ser Gly Arg Arg Cys Glu Val Arg Thr Ser
465                 470                 475                 480
Ile Asp Ala Cys Ala Ser Ser Pro Cys Phe Asn Arg Ala Thr Cys Tyr
                485                 490                 495
Thr Asp Leu Ser Thr Asp Thr Phe Val Cys Asn Cys Pro Tyr Gly Phe
            500                 505                 510
Val Gly Ser Arg Cys Glu Phe Pro Val Gly Leu Pro Pro Ser Thr Met
            515                 520                 525
Val Arg Ser Val Glu Cys Pro Pro Cys Pro Ala Pro Pro Val Ala Gly
```

```
                530                 535                 540
Pro Ser Val Phe Leu Phe Pro Lys Pro Lys Asp Thr Leu Met Ile
545                 550                 555                 560

Ser Arg Thr Pro Glu Val Thr Cys Val Val Val Asp Val Ser His Glu
                565                 570                 575

Asp Pro Glu Val Gln Phe Asn Trp Tyr Val Asp Gly Met Glu Val His
                580                 585                 590

Asn Ala Lys Thr Lys Pro Arg Glu Glu Gln Phe Asn Ser Thr Phe Arg
                595                 600                 605

Val Val Ser Val Leu Thr Val Val His Gln Asp Trp Leu Asn Gly Lys
                610                 615                 620

Glu Tyr Lys Cys Lys Val Ser Asn Lys Gly Leu Pro Ala Pro Ile Glu
625                 630                 635                 640

Lys Thr Ile Ser Lys Thr Lys Gly Gln Pro Arg Glu Pro Gln Val Tyr
                645                 650                 655

Thr Leu Pro Pro Ser Arg Glu Glu Met Thr Lys Asn Gln Val Ser Leu
                660                 665                 670

Thr Cys Leu Val Lys Gly Phe Tyr Pro Ser Asp Ile Ala Val Glu Trp
                675                 680                 685

Glu Ser Asn Gly Gln Pro Glu Asn Asn Tyr Lys Thr Thr Pro Pro Met
690                 695                 700

Leu Asp Ser Asp Gly Ser Phe Phe Leu Tyr Ser Lys Leu Thr Val Asp
705                 710                 715                 720

Lys Ser Arg Trp Gln Gln Gly Asn Val Phe Ser Cys Ser Val Met His
                725                 730                 735

Glu Ala Leu His Asn His Tyr Thr Gln Lys Ser Leu Ser Leu Ser Pro
                740                 745                 750

Gly Lys

<210> SEQ ID NO 8
<211> LENGTH: 157
<212> TYPE: PRT
<213> ORGANISM: Artificial Sequence
<220> FEATURE:
<223> OTHER INFORMATION: Human soluble TNF-alpha

<400> SEQUENCE: 8

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
                20                  25                  30

Ala Asn Ala Leu Leu Ala Asn Gly Val Glu Leu Arg Asp Asn Gln Leu
            35                  40                  45

Val Val Pro Ser Glu Gly Leu Tyr Leu Ile Tyr Ser Gln Val Leu Phe
        50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140
```

```
Ala Glu Ser Gly Gln Val Tyr Phe Gly Ile Ile Ala Leu
145                 150                 155

<210> SEQ ID NO 9
<211> LENGTH: 23
<212> TYPE: DNA
<213> ORGANISM: Artificial Sequence
<220> FEATURE:
<223> OTHER INFORMATION: Primer for detecting TCR rearrangement

<400> SEQUENCE: 9
caaggaaagg gaaaaaggaa gaa                                          23

<210> SEQ ID NO 10
<211> LENGTH: 21
<212> TYPE: DNA
<213> ORGANISM: Artificial Sequence
<220> FEATURE:
<223> OTHER INFORMATION: Primer for detecting TCR rearrangement

<400> SEQUENCE: 10
ttgcccctgc agttttttgta c                                           21

<210> SEQ ID NO 11
<211> LENGTH: 33
<212> TYPE: DNA
<213> ORGANISM: Artificial Sequence
<220> FEATURE:
<223> OTHER INFORMATION: Probe for detecting TCR rearrangement

<400> SEQUENCE: 11
atacgcacag tgctacaaaa cctacagaga cct                               33

<210> SEQ ID NO 12
<211> LENGTH: 21
<212> TYPE: DNA
<213> ORGANISM: Artificial Sequence
<220> FEATURE:
<223> OTHER INFORMATION: Primer for detecting TCR rearrangement

<400> SEQUENCE: 12
agcgggtggt gatggcaaag t                                            21

<210> SEQ ID NO 13
<211> LENGTH: 25
<212> TYPE: DNA
<213> ORGANISM: Artificial Sequence
<220> FEATURE:
<223> OTHER INFORMATION: Primer for detecting TCR rearrangement

<400> SEQUENCE: 13
ttagatggag gatgccttaa cctta                                        25

<210> SEQ ID NO 14
<211> LENGTH: 32
<212> TYPE: DNA
<213> ORGANISM: Artificial Sequence
<220> FEATURE:
<223> OTHER INFORMATION: Probe for detecting TCR rearrangement

<400> SEQUENCE: 14
cccgtgtgac tgtggaacca agtaagtaac tc                                32

<210> SEQ ID NO 15
<211> LENGTH: 25
```

```
<212> TYPE: DNA
<213> ORGANISM: Artificial Sequence
<220> FEATURE:
<223> OTHER INFORMATION: Primer for detecting TCR rearrangement

<400> SEQUENCE: 15
gacttggaga aaacatctgg ttctg                                            25
```